United States Patent
Messina et al.

(10) Patent No.: US 10,632,151 B2
(45) Date of Patent: *Apr. 28, 2020

(54) CANCER IMMUNOTHERAPY

(71) Applicant: University of Massachusetts, Boston, MA (US)

(72) Inventors: Louis M. Messina, Westborough, MA (US); Guodong Tie, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 147 days.

This patent is subject to a terminal disclaimer.

(21) Appl. No.: 15/538,690

(22) PCT Filed: Jan. 22, 2016

(86) PCT No.: PCT/US2016/014477
§ 371 (c)(1),
(2) Date: Jun. 22, 2017

(87) PCT Pub. No.: WO2016/118832
PCT Pub. Date: Jul. 28, 2016

(65) Prior Publication Data
US 2017/0368099 A1 Dec. 28, 2017

Related U.S. Application Data

(60) Provisional application No. 62/106,507, filed on Jan. 22, 2015.

(51) Int. Cl.
*C12N 5/00* (2006.01)
*C12N 5/02* (2006.01)
*A61K 35/17* (2015.01)
*C12N 5/0783* (2010.01)
*A61P 35/00* (2006.01)
*A61K 35/12* (2015.01)

(52) U.S. Cl.
CPC ............ *A61K 35/17* (2013.01); *A61P 35/00* (2018.01); *C12N 5/0646* (2013.01); *A61K 2035/124* (2013.01); *C12N 2501/65* (2013.01); *C12N 2501/70* (2013.01); *C12N 2501/998* (2013.01); *C12N 2510/00* (2013.01)

(58) Field of Classification Search
None
See application file for complete search history.

(56) References Cited

U.S. PATENT DOCUMENTS

| | | |
|---|---|---|
| 7,741,345 B2 | 6/2010 | Cannizzaro et al. |
| 8,790,655 B2 | 7/2014 | Carson et al. |
| 8,795,678 B2 | 8/2014 | Liang |
| 10,034,901 B2 | 7/2018 | Messina |
| 2011/0236362 A1 | 9/2011 | Watarai et al. |
| 2011/0236894 A1 | 9/2011 | Rao et al. |
| 2012/0190731 A1 | 7/2012 | Messina et al. |
| 2012/0272346 A1 | 10/2012 | Stillman et al. |
| 2013/0323220 A1 | 12/2013 | Joung et al. |
| 2015/0153349 A1 | 6/2015 | Galon et al. |

FOREIGN PATENT DOCUMENTS

| | | |
|---|---|---|
| WO | WO 2007135195 | 11/2007 |
| WO | WO 2009/114547 | 9/2009 |
| WO | WO 2009/146399 | 12/2009 |
| WO | WO 2013/173223 | 11/2013 |
| WO | WO 2015/113922 | 8/2015 |
| WO | WO 2016/109668 | 7/2016 |

OTHER PUBLICATIONS

Bendelac et al., "The biology of NKT cells," Annu Rev Immunol, 2007, 25:297-336.
Bennouna et al., "Phase I study of bromohydrin pyrophosphate (BrHPP, IPH 1101), a Vγ9Vδ2 T lymphocyte agonist in patients with solid tumors," Cancer Immunol Immunother, 2010, 59:1521-1530.
Bryder et al. Interleukin-3 supports expansion of long-term multilineage repopulating activity after multiple stem cell divisions in vitro. Blood. 96:1748-1755 (2000).
Chen et al., "TET2 promotes histone O-G1cNAcylation during gene transcription," Nature, 2013, 493(7433):561-564.
Chien et al., "γδ T cells: first line of defense and beyond," Annu Rev Immunol, 2014, 32:121-155.
Cimmino et al., " TETI is a tumor suppressor of hematopoietic malignancy," Jun. 2015, Nat Immunol, 16:653-62.
Crowe et al., "A Critical Role for Natural Killer T Cells in Immunosurveillance of Methylcholanthrene-induced Sarcomas," J Exp Med, 2002, 196:119-127.
Cullen et al., "Hematopoietic stem cell development: an epigenetic journey," Curr Top Dev Biol, 2014, 107:39-75.
Deplus et al., "TET2 and TET3 regulate GlcNAcylation and H3Kr Methylation through OCT and SET1/COMPASS," Embo J, 2013, 32:645-655.
Fisher et al., "γδ cells for cancer immunotherapy: A systematic review of clinical trials," Oncoimmunology, 2014, 3: e27572.
Garbe et al., "TCR and Notch synergize in αβ versus γδ lineage choice," Trends Immunol, 2007, 28:124-131.
Godfrey et al., "NKT cells: what's in a name?," Nat Rev Immunol, 2004, 4:231-237.

(Continued)

*Primary Examiner* — Michail A Belyavskyi
(74) *Attorney, Agent, or Firm* — Fish & Richardson P.C.

(57) ABSTRACT

Methods of providing populations of NKT and/or γδ T cells, and their use, e.g., in therapies such as cancer immunotherapy.

6 Claims, 16 Drawing Sheets
Specification includes a Sequence Listing.

(56) References Cited

OTHER PUBLICATIONS

Gomes et al., "Targeting γδ T lymphocytes for cancer immunotherapy: from novel mechanistic insight to clinical application," Cancer Res, 2010, 70:10024-7.
Greten et al., "IKKβ Links Inflammation and Tumorigenesis in a Mouse Model of Colitis-Associated Cancer," Cell, 2004, 118:285-296.
Holtmeier et al., "γδ T cells link innate and adaptive immune responses," Chem Immunol Allergy, 2005, 86:151-183.
International Preliminary Report on Patentability in International Application No. PCT/US2016/014477, dated Jul. 25, 2017, 9 pages.
Ito et al., "Role of Tet proteins in 5mC to 5hmC conversion, ES cell self-renewal, and ICM specification," Nature, 2010, 466:1129-1133.
Ito et al., "Tet proteins can convert 5-methylcytosine to 5-formylcytosine and 5-carboxylcytosine," Science, 2011, 333:1300-1303.
Ko et al., "Impaired hydroxylation of 5-methylcytosine in myeloid cancers with mutant TET2," Nature, 2010, 468:839-843.
Ko et al., "Ten-Eleven-Translocation 2 (TET2) negatively regulates homeostasis and differentiation of hematopoietic stem cells in mice," PNAS, 2011, 108:14566-14571.
Kobayashi H, et al. A New Indicated of Favorable Prognosis in Locally Advanced Renal Cell Carcinomas: γδ T-Cells in Peripheral Blood. Anticancer Research 31:1027-1032 (2011).
Kobayashi et al., "Safety profile and anti-tumor effects of adoptive immunotherapy using gamma-delta T cells against advanced renal cell carcinoma: a pilot study," Cancer Immunol Immunother, 2007,. 56:469-476.
Kondo et al., "Zoledronate facilitates large-scale ex vivo expansion of functional γδ T cells from cancer patients for use in adoptive immunotherapy," Cytotherapy, 2008, 10:842-856.
Lantz et al., "An invariant T cell receptor α chain is used by a unique subset of major histocompatibility complex class I-specific $CD4^+$ and $CD4^-8^-$ T cells in mice and humans," J Exp Med, 1994, 180:1097-1106.
Matsuda et al., "Developmental program of mouse Valpha14i NKT cells," Curr Opin Immunol, 2005, 17:122-130.
Motohashi et al., "A Phase I Study of In vitro Expanded Natural Killer T Cells in Patients with Advanced and Recurrent Non-Small Cell Lung Cancer," Clin Cancer Res, 2006, 12:6079-6086.
Notification of the International Search Report and Written Opinion of the International Searching Authority, or the Declaration, International Application No. PCT/US16/14477, dated Apr. 22, 2016, 15 pages.
Porcelli et al., "Analysis of T cell antigen receptor (TCR) expression by human peripheral blood $CD4^-8^-$ αβ T cells demonstrates preferential use of several Vβ genes and an invariant TCR α chain," J Exp Med, 1993, 178:1-16.
Rector et al., "Comprehensive Hematopoietic Stem Cell Isolation Methods," Methods Mol Biol, 2013, 976:1-15.
Rogers et al., "A role for DNA hypomethylation and histone acetylation in maintaining allele-specific expression of mouse NKG2A in developing and mature NK cells," J Immunol, 2006, 177(1):414-21.
Shi et al., "Ten-Eleven Translocation 1 (TET1) Is Regulated by O-Linked N-Acetylglucosamine Transferase (Ogt) for Target Gene Repression in Mouse Embryonic Stem Cells," J Biol Chem, 2013, 288:20776-20784.
Smyth et al., "Tumor necrosis factor-related apoptosis-inducing ligand (TRAIL) contributes to interferon gamma-dependent natural killer cell protection from tumor metastasis," J Exp Med, 2001, 193:661-670.
Taniguchi et al., "The NKT cell system: bridging innate and acquired immunity," Nature Immunology, 2003, 4:1164-1165.
Themeli et al., "Generation of tumor-targeted human T lymphocytes from induced pluripotent stem cells for cancer therapy," Nat Biotechnol, 2013, 31:928-933.
Todaro et al., "Efficient Killing of Human Colon Cancer Stem Cells by γδ T Lymphocytes," J Immunol, 2009, 182-7287-7296.
Toura et al., "Cutting Edge: Inhibition of Experimental Tumor Metastasis by Dendritic Cells Pulsed with α-Galactosylceramide," J Immunol, 1999, 163: 2387-2391.
Vella et al., "Tet proteins connect the O-linked N-acetylglucosamine transferase Ogt to chromatin in embryonic stem cells," Mol Cell, 2013, 49:645-656.
Watarai et al., "Murine induced pluripotent stem cells can be derived from and differentiate into natural killer T cells," J Clin Invest, 2010, 120(7):2610-2618.
Wu et al., "Mechanisms and functions of Tet protein-mediated 5-methylcytosine oxidation," Genes Dev, 2011, 25:2436-2452.
Yokota et al., "Complementary regulation of early B-lymphoid differentiation by genetic and epigenetic mechanisms," Int. J. Hematol, 2013, 98:382-389.
European Search Report and Written Opinion in International Application No. 16740821.0, dated Jul. 25, 2018, 8 pages.
Spanholtz et al., "High Log-Scale Expansion of Functional Human Natural Killer Cells from Umbilical Cord Blood CD34-Positive Cells for Adoptive Cancer Immunotherapy," Plos One, Feb. 2010, 5: e9221.
Wu et al., "Suppression of TET1-Dependent DNA Demethylation Is Essential for KRAS-Mediated Transformation," Cell Reports, Dec. 2014, 9: 1827-1840.
Alder et al., "Kruppel-like factor 4 is essential for inflammatory monocyte differentiation in vivo," J. Immunol., Apr. 2008, 180:5645-5652.
Alexandrescu et al., "Immunotherapy for Melanoma: Current Status and Perspectives," J. Immunother., Jul.-Aug. 2010, 33(6):570-590.
American Diabetes Association, "2. Classification and Diagnosis of Diabetes," Diabetes Care, 2015, 38(Supplement 1):S8-S16.
American Diabetes, "11. Older Adults: Standards of Medical Care in Diabetes—2018," Diabetes Care, 2018, 41(Suppl 1):S119-S125.
Bannon et al., "Diabetes induces stable intrinsic changes to myeloid cells that contribute to chronic inflammation during wound healing in mice," Dis. Model Mech., Nov. 2013, 6(6):1434-1447.
Bedard and Krause, "The NOX family of ROS-generating NADPH oxidases: physiology and pathophysiology," Physiol. Rev., Jan. 2007, 87(1):245-313.
Berezhnoy et al., "A clinically useful approach to enhance immunological memory and antitumor immunity," Oncoimmunology, May 2014, 14(3):e28811-3.
Boesch et al., "Heterogeneity of cancer stem cells: rationale for targeting the stem cell niche," Biochimica Biophysica Acta, Dec. 2016, 1866(2):276-289.
Bollino and Webb, "Chimeric antigen receptor-engineered natural killer and natural killer T cells for cancer immunotherapy," Transl. Res., Sep. 2017, 187:32-43.
Bonomini et al., "Metabolic syndrome, aging and involvement of oxidative stress," Aging Dis., Mar. 2015, 6(2):109-120.
Boulton et al., "The global burden of diabetic foot disease," Lancet, Nov. 2005, 366(9498):1719-1724.
Brem and Tomic-Canic, "Cellular and molecular basis of wound healing in diabetes," J. Clin. Invest., May 2007, 117(5):1219-1222.
Brem et al., "Evidence-based protocol for diabetic foot ulcers," Plast. Reconstr. Surg., Jun. 2006, 117(7 Suppl):193S-209S.
Brem et al., "The synergism of age and db/db genotype impairs wound healing," Exp. Gerontol., Jun. 2007, 42(6):523-531.
Breslin et al., "Mouse blood monocytes: Standardizing their identification and analysis using CD11," J. Immunol. Methods., Apr. 2013, 390(1-2):1-8.
Buttigieg et al., "NOX2 (gp91phox) is a predominant O2 sensor in a human airway chemoreceptor cell line: biochemical, molecular, and electrophysiological evidence," Am. J. Physiol. Lung Cell. Mol. Physiol., Oct. 2012, 303(7):L598-L607.
Caravaggi et al., "Management of ischemic diabetic foot," J. Cardiovasc., Surg., Dec. 2013, 54(6):737-754.
Castellano et al., "Constrained analogues of procaine as novel small molecule inhibitors of DNA methyltransferase-1," J. Med. Chem., Apr. 2008, 51(7): 2321-2325.
Castillo-Aguilera et al., "DNA methylation targeting: the DNMT/HMT crosstalk challenge," Biomolecules, Mar. 2017, 7(1): 3.
Chambers et al., "Aging hematopoietic stem cells decline in function and exhibit epigenetic dysregulation," PLoS Biol., Aug. 2007, 5(8):e201:1750-1762.

(56) References Cited

OTHER PUBLICATIONS

Chapman et al., "TET-catalyzed 5-hydroxymethylcytosine regulates gene expression in differentiating colonocytes and colon cancer," Sci Rep., Dec. 2015, 5:17568.
Chen et al., "Absence of CD4 or CD8 lymphocytes changes infiltration of inflammatory cells and profiles of cytokine expression in skin wounds, but does not impair healing," Exp. Dermatol., Mar. 2014, 23(3):189-194.
Choo et al., "MicroRNA-5p and -3p co-expression and cross-targeting in colon cancer cells," J. Biomed. Sci., Oct. 2014, 21:95, 14 pages.
Cieslewicz et al., "Targeted delivery of proapoptotic peptides to tumor-associated macrophages improves survival," PNAS, Oct. 2013, 110(40):15919-15924.
Coffman et al., "Endothelin receptor-A is required for the recruitment of antitumor T cells and modulates chemotherapy induction of cancer stem cells," Cancer Biol. Ther., Feb. 2013, 14(2):184-192.
Corpuz et al., "Differential responsiveness of Innate-like IL-17- and IFN-γ-producing γδ T cells to homeostatic cytokines," J. Immunol., Jan. 2016, 196(2):645-654.
Cubbon et al., "Effects of insulin resistance on endothelial progenitor cells and vascular repair," Clin. Sci., Aug. 2009, 117(5):173-190.
Cui et al., "Upregulated lncRNA SNHG1 contributes to progression of non-small cell lung cancer through inhibition of mlR-101-3p and activation of Wnt/P-catenin signaling pathway," Oncotarget, Mar. 2017, 8(11): 17785-17794.
Daigneault et al., "The identification of markers of macrophage differentiation in PMA-stimulated THP-1 cells and monocyte-derived macrophages," PLoS One, Jan. 2010, 5(1):e8668, 31 pages.
Dakic et al., "PU.1 regulates the commitment of adult hematopoietic progenitors and restricts granulopoiesis," J. Exp. Med., May 2005, 201(9):1487-1502.
Dhodapkar et al., "A reversible defect in natural killer T cell function characterizes the progression of premalignant to malignant multiple myeloma," J Exp. Med., Jun. 2003, 197(12):1667-1676.
Diebold et al., "NOX2 as a target for drug development: indications, possible complications, and progress," Antioxid. Redox. Signal., Aug. 2015, 23(5):375-405.
Dieterlen-Lievre, "Hematopoiesis: progenitors and their genetic program," Curr. Biol., Oct. 1998, 8(20):R727-R730.
Donovan et al., "Drugs for gestational diabetes," Australian Prescriber, Oct. 2010, 33(5):141-144.
Drechsler et al., "Hyperlipidemia-triggered neutrophilia promotes early atherosclerosis," Circulation, Nov. 2010, 122(18):1837-1845.
Dunn et al., "Cancer immunoediting: from immunosurveillance to tumor escape," Nat. Immunol., Nov. 2002, 3(11):991-998.
Dunn et al., "Interferons, immunity and cancer immunoediting," Nat. Rev. Immunol., Nov. 2006, 6(11): 836-848.
Dunn et al., "The immunobiology of cancer immunosurveillance and immunoediting," Immunity, Aug. 2004, 21(2):137-148.
Eggermont et al., "Anti-CTLA-4 antibody adjuvant therapy in melanoma," Semin. Oncol., Oct. 2010, 37(5):455-459.
Ensembl. Gene: DNMT1 ENSMUSG00000004099. Jul. 2018; downloaded from the internet <https://uswest.ensembl.org/Mus_musculus/Gene/Sequence?g=ENSMUSG00000004099;r=9:20907209-20959888> on Sep. 21, 2018, pp. 1-16.
Escamilla-Tilch et al., "The interplay between pathogen-associated and danger-associated molecular patterns: an inflammatory code in cancer?," Immunol. Cell Biol., Nov.-Dec. 2013, 91(10):601-610.
Esteve et al., "Direct interaction between DNMT1 and G9a coordinates DNA and histone methylation during replication," Genes Dev., Nov. 2006, 20(22):3089-3103.
Fadini et al., "An unbalanced monocyte polarisation in peripheral blood and bone marrow of patients with type 2 diabetes has an impact on microangiopathy," Diabetologia, Aug. 2013, 56:(8):1856-1866.
Fagan et al., "Laccaic acid A is a direct DNA-competitive inhibitor of DNA methyltransferase 1," J. Biol. Chemistry, Aug. 2013, 288(33):23858-23867.
Falanga, "Wound healing and its impairment in the diabetic foot," Lancet, Nov. 2005, 366(9498):1736-1743.
Fan et al., "DNA methyltransferase 1 knockdown induces silenced CDH1 gene reexpression by demethylation of methylated CpG in hepatocellular carcinoma cell line SMMC-7721," Eur. J. Gastroenterol. Hepatol., Nov. 2007, 19(11):952-961.
Feinberg et al., "The Kruppel-like factor KLF4 is a critical regulator of monocyte differentiation," EMBO J., Sep. 2007, 26(18):4138-4148.
Folli et al., "Altered insulin receptor signalling and β-cell cycle dynamics in type 2 diabetes mellitus," PLoS One, 2011, 6(11):e28050, 11 pages.
Font-Burgada et al., "Obesity and cancer: the oil that feeds the flame," Cell Metab., Jan. 2016, 23(1):48-62.
Foulks et al., "Epigenetic drug discovery: targeting DNA methyltransferases," J. Biol. Screen., Jan. 2012, 17(1):2-17.
Francke et al., "Generation of mature murine monocytes from heterogeneous bone marrow and description of their properties," J. Histochem. Cytochem., Sep. 2011, 59(9):813-825.
Frank et al., "Autophagic digestion of *Leishmania major* by host macrophages is associated with differential expression of BNIP3, CTSE, and the miRNAs miR-101c, miR-129, and miR-210," Parasit. Vectors, Jul. 2015, 8:404.
Gallagher et al., "Epigenetic changes in bone marrow progenitor cells influence the inflammatory phenotype and alter wound healing in type 2 diabetes," Diabetes, Apr. 2015, 64(4):1420-1430.
Galluzi et al., "Trial watch: experimental Toll-like receptor agonists for cancer therapy," Oncoimmunol., Aug. 2012, 1(5): 699-716.
Galon et al., "Cancer classification using the immunoscore: a worldwide task force," J. Transl. Med., Oct. 2012, 10:205-214.
Ganesan and Bakhshi, "Systemic therapy for melanoma," Natl. Med. J. India., 2010, 23(1):21-7.
Gangaraju and Lin, "MicroRNAs: key regulators of stem cells," Nat. Rev. Mol. Cell. Biol., Feb. 2009, 10(2):116-125.
Geiger et al., "Hematopoietic stem cell aging," Curr. Opin. Immunol., Aug. 2014, 29:86-92.
Geissmann et al., "Development of monocytes, macrophages, and dendritic cells," Science, Feb. 2010, 327(5966):656-661.
Georgantas et al., "Microarray and serial analysis of gene expression analyses identify known and novel transcripts overexpressed in hematopoietic stem cells," Cancer Res., Jul. 2004, 64(13):4434-4441.
Gerstein et al., "Wound healing and aging," Dermatol.Clin., Oct. 1993, 11(4):749-757.
Gilbert et al., "DNA methylation affects nuclear organization, histone modifications, and linker histone binding but not chromatin compaction," J. Cell Biol., May 2007, 177(3):401-411.
Golovina and Vonderheide, "Regulatory T cells: overcoming suppression of T-cell immunity," Cancer J., Jul.-Aug. 2010, 16(4):342-347.
Gore et al., "DNA methylation in hematopoietic development and disease," Exp. Hematol, Sep. 2016, 44(9):783-790.
Gosain et al., "Aging and wound healing," World J. Surg., Mar. 2004, 28(3):321-326.
Gould & Fulton, "Wound healing in older adults," R.I. Med. J., Feb. 2016, 99(2): 34-36.
Gould et al., "Chronic wound repair and healing in older adults: current status and future research," J. Am. Geriatr. Soc., Mar. 2015, 63(3):427-438.
Guo and Dipietro, "Factors affecting wound healing," J. Dent. Res., Mar. 2010, 89(3): 219-229.
Guo et al., "Cancer stem cells," Pediatric Res., Apr. 2006, 59(4 Pt 2):59R-64R.
Guo et al., "Mapping cellular hierarchy by single-cell analysis of the cell surface repertoire," Cell Stem Cell, Oct. 2013, 13(4):492-505.
Haetscher et al., "STAT5-regulated microRNA-193b controls haematopoietic stem and progenitor cell expansion by modulating cytokine receptor signalling," Nat. Commun., Nov. 2015, 6:8928, 11 pages.
Hennekens and Andreotti, "Leading avoidable cause of premature deaths worldwide: case for obesity," Am. J. Med., Feb. 2013, 126(2):97-98.

(56) References Cited

OTHER PUBLICATIONS

Hirano et al., "Discovery of GSK2795039, a novel small molecule NADPH oxidase 2 inhibitor," Antioxid. Redox. Signal., Aug. 2015, 23(5):358-374.
Holmes and Zuniga-Pflucker, "The OP9-DL1 system: generation of T-lymphocytes from embryonic or hematopoietic stem cells in vitro," Cold Spring Harb. Protoc., Feb. 2009, 2009(2):pdb.prot5156.
Huang et al., "Rates of complications and mortality in older patients with diabetes mellitus," JAMA Intern. Med., Feb. 2014, 174(2):251-258.
Huber et al., "Regulation of monocyte differentiation by specific signaling modules and associated transcription factor networks," Cell. Mol. Life Sci., Jan. 2014, 71(1):63-92.
International Search Report and Written Opinion in International Application No. PCT/US17/59367, dated Feb. 2, 2019.
International Search Report and Written Opinion in International Application No. PCT/US18/40642 dated Nov. 5, 2018, 16 pages.
Jablonski et al., "Novel markers to delineate murine M1 and M2 macrophages," PLoS One, Dec. 2015, 10(12):e0145342, 25 pages.
Jackson et al., "Severe global DNA hypomethylation blocks differentiation and induces histone hyperacetylation in embryonic stem cells," Mol. Cell. Biol., Oct. 2004, 24(20):8862-8871.
Jin et al., "DNA methyltransferase 3B (DNMT3B) mutations in ICF syndrome lead to altered epigenetic modifications and aberrant expression of genes regulating development, neurogenesis and immune function," Hum. Mol. Genet., Mar. 2008, 17(5):690-709.
Jin et al., "Long non-coding RNA SPRY4-IT1 promotes proliferation and invasion by acting as a ceRNA of miR-101-3p in colorectal cancer cells," Tumour Biol., Jul. 2017, 39(7): 1-6.
Katsarou et al., "Type 1 diabetes mellitus," Nat. Rev. Dis. Primers, Mar. 2017, 3:17016, 17 pages.
Kawasaki and Taira, "Induction of DNA methylation and gene silencing by short interfering RNAs in human cells," Nature, Sep. 2004, 431(7005):211-217.
Kerkar et al., "Cellular constituents of immune escape within the tumor microenvironment," Cancer Res., Jul. 2012, 72(13): 3125-3130.
Khanna et al., "Macrophage dysfunction impairs resolution of inflammation in the wounds of diabetic mice," PLoS One, Mar. 2010, 5(3):e9539, 12 pages.
Kim et al., "Discrete Notch signaling requirements in the specification of hematopoietic stem cells," EMBO J., Oct. 2014, 33(20):2363-2373.
Klein et al., "Mutations in DNMT1 cause hereditary sensory neuropathy with dementia and hearing loss," Nat. Genet., Jun. 2011, 43(6):595-600.
Klingenberg et al., "Depletion of FOXP3+ regulatory T cells promotes hypercholesterolemia and atherosclerosis," J. Clin. Invest., Mar. 2013, 12(3)3:1323-1334.
Klinke, "A multiscale systems perspective on cancer, immunotherapy, and Interleukin-12," Mol. Cancer., Sep. 2010, 9:242, 18 pages.
Koene et al., "Shared risk factors in cardiovascular disease and cancer," Circulation, Mar. 2016, 133(11):1104-1114.
Krüger et al., "Immune based therapies in cancer," Histol Histopathol., Jun. 2007, 22(6):687-696.
Krzyszczyk et al., "The role of macrophages in acute and chronic wound healing and interventions to promote pro-wound healing phenotypes," Front. Physiol., May 2018, 9:419, 22 pages.
Kurita et al., "DNMT1 and DNMT3b silencing sensitizes human hepatoma cells to TRAIL-mediated apoptosis via up-regulation of Trail-R2/DR5 and caspase-8," Cancer Sci., Jun. 2010, 101(6):1431-1439.
Laslo et al., "Multilineage transcriptional priming and determination of alternate hematopoietic cell fates," Cell, Aug. 2006, 126(4):755-766.
Lee and Margolin, "Cytokines in Cancer Immunotherapy," Cancers, Oct. 2011, 3(4):3856-3893.
Li et al., "Epigenetic inactivation of the CpG demethylase TET1 as a DNA methylation feedback loop in human cancers," Sci. Rep., May 2016, 6:26591, 13 pages.
Li et al., "Targeted mutation of the DNA methyltransferase gene results in embryonic lethality," Cell, Jun. 1992, 69(6):915-926.
Li et al., "Tumor microenvironment: the role of tumor stroma in cancer," J. Cell. Biochem., Jul. 2007, 101(4):805-815.
Liao et al., "Krüppel-like factor 4 regulates macrophage polarization," J. Clin. Invest., Jul. 2011, 121(7):2736-2749.
Liao et al., "Targeted disruption of DNMT1, DNMT3A and DNMT3B in human embryonic stem cells," Nat. Genet., May 2015, 47(5):469-478.
Liguori et al., "Oxidative stress, aging, and diseases," Clin. Interv. Aging, Apr. 2018, 13:757-772.
Liu et al., "Age-dependent impairment of HIF-1a expression in diabetic mice: correction with electroporation-facilitated gene therapy increases wound healing, angiogenesis, and circulating angiogenic cells," J. Cell. Physiol., Nov. 2008, 217(2):319-327.
Liu et al., "MicroRNA-101-3p suppresses cell proliferation, invasion and enhances chemotherapeutic sensitivity in salivary gland adenoid cystic carcinoma by targeting Pim-1," Am. J. Cancer Res., Oct. 2015, 5(10): 3015-3029.
Lu et al., "Polysaccharide krestin is a novel TLR2 agonist that mediates inhibition of tumor growth via stimulation of CD8 T Cells and NK Cells," Clin. Cancer. Res., Jan. 2011, 17(1):67-76.
Luo et al., "Long non-coding RNAs control hematopoietic stem cell function," Cell Stem, Apr. 2015, 16(4):426-438.
Luo, et al., "Targeting tumor-associated macrophages as a novel strategy against breast cancer," J. Clin. Invest., Aug. 2006, 116(8):2132-2141.
MacLeod et al., "Skin-resident T cells sense ultraviolet radiation-induced injury and contribute to DNA repair," J. Immunol., Jun. 2014, 192(12):5695-5702.
Makrantonaki et al., "Pathogenesis of wound healing disorders in the elderly," J. Dtsch Dermatol. Ges., Mar. 2017, 15(3):255-275.
Mantovani et al., "Macrophage polarization comes of age," Immunity, Oct. 2005, 23(4):344-346.
Martinez et al., "Alternative activation of macrophages: an immunologic functional perspective," Annu Rev. Immunol., 2009, 27:451-483.
Maruyama et al., "Decreased macrophage No. and activation lead to reduced lymphatic vessel formation and contribute to impaired diabetic wound healing," Am. J. Pathol., Apr. 2007, 170(4): 1178-1191.
McKercher et al., "Targeted disruption of the PU.1 gene results in multiple hematopoietic abnormalities," EMBO J., Oct. 1996, 15(20):5647-5658.
Melero et al., "IL-12 gene therapy for cancer:in synergy with other immunotherapies," Trends. Immunol., Mar. 2001, 22(3):113-115.
Mercer et al., "Multilineage priming of enhancer repertoires precedes commitment to the B and myeloid cell lineages in hematopoietic progenitors," Immunity, Sep. 2011, 35(3):413-425.
Mineharu et al., "Blockade of mTOR signaling via rapamycin combined with immunotherapy augments antiglioma cytotoxic and memory T-Cell Functions," Mol. Cancer Ther., Dec. 2014, 13(12): 3024-3036.
Moschella et al., "Combination strategies for enhancing the efficacy of immunotherapy in cancer patients," Ann. NY Acad. Sci., Apr. 2010, 1194:169-178.
Munn, "Blocking IDO activity to enhance anti-tumor immunity," Front Biosci (Elite Ed), Jan. 2012, 4: 734-745.
NCEP, "Third Report of the National Cholesterol Education Program (NCEP) Expert Panel on Detection, Evaluation, and Treatment of High Blood Cholesterol in Adults (Adult Treatment Panel III) final report," Circulation, 2002, 106(25): 3143-421.
Neri et al., "TET1 is a tumour suppressor that inhibits colon cancer growth by derepressing inhibitors of the WNT pathway," Oncogene, Aug. 2015, 34(32): 4168-4176.
Notarnicola et al., "Serum lipid profile in colorectal cancer patients with and without synchronous distant metastases," Oncology, 2005, 68(4-6):371-374.

(56) References Cited

OTHER PUBLICATIONS

Nunez-Cruz et al., "Differential requirement for the SAP-Fyn interaction during NK T cell development and function," J. Immunol., Aug. 2008, 181(4):2311-2320.
Oh et al., "Stem cell aging: mechanisms, regulators and therapeutic opportunities," Nat. Med., Aug. 2014, 20(8):870-880.
Okano et al., "Cloning and characterization of a family of novel mammalian DNA (cytosine-5) methyltransferases," Nat. Genet., Jul. 1998, 19(3): 219-220.
Okano et al., "DNA methyltransferases Dnmt3a and Dnmt3b are essential for de novo methylation and mammalian development," Cell, Oct. 1999, 99(3):247-257.
Omar et al., "Enhanced beta cell function and anti-inflammatory effect after chronic treatment with the dipeptidyl peptidase-4 inhibitor vildagliptin in an advanced-aged diet-induced obesity mouse model," Diabetologia, Aug. 2013. 56(8):1752-1760.
Orkin, "Priming the hematopoietic pump," Immunity, Nov. 2003, 19(5):633-634.
Outtz et al., "Notch1 deficiency results in decreased inflammation during wound healing and regulates vascular endothelial growth factor receptor-1 and inflammatory cytokine expression in macrophages," J. Immunol., Oct. 2010, 185(7):4363-4373.
Papakonstantinou et al., "Differential microRNA profiles and their functional implications in different immunogenetic subsets of chronic lymphocytic leukemia," Mol. Med., May 2013, 19: 115-123.
Pattabiraman and Weinberg, "Tackling the cancer stem cells—what challenges do they pose?," Nat. Rev. Drug Discov., Jul. 2014, 13(7):497-512.
PCT International Preliminary Report On Patentability in International Application No. PCT/US17/59367, dated May 16, 2019, 11 pages.
Pearce et al., "Enhancing CD8 T-cell memory by modulating fatty acid metabolism," Nature, Jul. 2009, 460(7251):103-107.
Pervaiz et al., "Oxidative stress regulation of stem and progenitor cells," Antioxid. Redox. Signal., Nov. 2009, 11(11):2777-2789.
Piccoli et al., "Bone-marrow derived hematopoietic stem/progenitor cells express multiple isoforms of NADPH oxidase and produce constitutively reactive oxygen species," Biochem. Biophys. Res. Commun., Feb. 2007, 353(4):965-972.
Plowden et al., "Innate immunity in aging: impact on macrophage function," Aging Cell, Aug. 2004, 3(4):161-167.
Portielje et al., "IL-12: a promising adjuvant for cancer vaccination," Cancer Immunol. Immunother., Mar. 2003, 52(3):133-144.
Pradeu and Cooper, "The danger theory: 20 years later," Front Immunol., 2012, 3:287, 10 pages.
Prattichizzo et al., "'Inflammaging' as a druggable target: a senescence-associated secretory phenotype-centered view of type 2 diabetes," Oxid Med Cell. Longev., vol. 2016, Article ID 1810327, 10 pages.
Quail and Joyce, "Microenvironmental regulation of tumor progression and metastasis," Nature Medicine, Nov. 2013, 19(11):1423-1437.
Reiber et al., "Causal pathways for incident lower-extremity ulcers in patients with diabetes from two settings," Diabetes Care, Jan. 1999, 22(1):157-162.
Robson et al., "Oxidative stress biomarkers in type 2 diabetes mellitus for assessment of cardiovascular disease risk," Diabetes Metab. Syndr., May 2018, 12(3):455-462.
Sag et al., "ATP-binding cassette transporter G1 intrinsically regulates invariant NKT cell development," J. Immunol., Dec. 2012, 189(11):5129-5138.
Sag et al., "The cholesterol transporter ABCG1 links cholesterol homeostasis and tumour immunity," Nat. Commun., Feb. 2015, 6:6354, 14 pages.
Satoh et al., "Unbalanced M1/M2 phenotype of peripheral blood monocytes in obese diabetic patients: effect of pioglitazone," Diabetes Care, Jan. 2010, 33(1):e7.
Schmitt et al., "Induction of T cell development and establishment of T cell competence from embryonic stem cells differentiated in vitro," Nat. Immunol., Apr. 2004, 5(4):410-417.

Schroeder et al., "Notch signaling induces multilineage myeloid differentiation and up-regulates PU.1 expression," J. Immunol., Jun. 2003, 170(11):5538-5548.
Scott et al., "Antibody therapy of cancer," Nature Reviews Cancer, Mar. 2012, 12(4):278-287.
Sesti et al., "Insulin receptor variant forms and Type 2 diabetes mellitus," Pharmacogenomics, Feb. 2000, 1(1):49-61.
Sesti et al., "Molecular mechanism of insulin resistance in type 2 diabetes mellitus: role of the insulin receptor variant forms," Diabetes Metab. Res. Rev., Sep.-Oct. 2001, 17(5):363-373.
Sgonc et al., "Age-related aspects of cutaneous wound healing: a mini-review," Gerontology, 2013, 59(2):159-164.
Shah et al., "DNMT3A mutations in acute myeloid leukemia," Nat. Genet., Mar. 2011, 43(4):289-290.
Shiao et al., "Immune microenvironments in solid tumors: new targets for therapy," Genes & Dev., Dec. 2011, 25(24):2559-2572.
Shibata et al., "Adiponectin regulates psoriasiform skin inflammation by suppressing IL-17 production from γδ-T cells," Nat. Commun., Jul. 2015, 6:7687, 14 pages.
Shultz et al., "Human lymphoid and myeloid cell development in NOD/LtSz-scid IL2R null mice engrafted with mobilized human hemopoietic stem cells," J. Immunol., May 2005, 174(10): 6477-6489.
Silva-Santos et al., "γδ T cells in cancer," Nat. Rev. Immunol., Nov. 2015, 15(11):883-889.
Sosenko et al., "The prediction of type 1 diabetes by multiple autoantibody levels and their incorporation into an autoantibody risk score in relatives of type 1 diabetic patients," Diabetes Care, Sep. 2013, 36(9):2615-2620.
Strid et al., "Acute upregulation of an NKG2D ligand promotes rapid reorganization of a local immune compartment with pleiotropic effects on carcinogenesis," Nat. Immunol., Feb. 2008, 9(2):146-154.
Tarhini and Iqbal, "CTLA-4 blockade: therapeutic potential in cancer treatments," Onco. Targets Ther., Jun. 2010, 3:15-25.
Tavares et al., "Normal lymphocyte immunophenotype in an elderly population," Rev. Bras. Hematol. Hemoter., May-Jun. 2014, 36(3):180-183.
Tepper et al., "Decreased circulating progenitor cell number and failed mechanisms of stromal cell-derived factor-1 mediated bone marrow mobilization impair diabetic tissue repair," Diabetes, Aug. 2010, 59(8):1974-1983.
Thermofisher Scientific, "hsa-miR-132-3p Product Details," Jan. 2, 2018; downloaded from the internet <https://https://www.thermofisher.com/order/genome-database/details/mirna/MC10166>, pp. 1-3.
Tie et al., "Hypercholesterolemia induces oxidant stress that accelerates the ageing of hematopoietic stem cells," J Am Heart Assoc., Jan. 2014, 3(1):e000241.
Topalian et al., "Safety, activity, and immune correlates of anti-Pd-1 antibody in cancer," NEJM, Jul. 2012, 366(26):2443-2454.
TPA: Mus msuculus mRNA mmu-let-7d-3p; GenBank Accession LM379002.1. Mar. 3, 2015; downloaded from the internet <https://www.ncbi.nlm.nih.gov/nuccore/LM379002> on Sep. 25, 2018, p. 2.
Trowbridge et al., "DNA methyltransferase 1 is essential for and uniquely regulates hematopoietic stem and progenitor cells," Cell Stem Cell, Oct. 2009, 5(4):442-449.
Turley et al., "Immunological hallmarks of stromal cells in the tumor microenvironment," Nat. Rev. Immunol., Nov. 2015, 15(11):669-682.
Van Galen et al., "Reduced lymphoid lineage priming promotes human hematopoietic stem cell expansion," Cell Stem Cell, Jan. 2014, 14(1):94-106.
Vantourout and Hayday, "Six-of-the-best: unique contributions of γδ T cells to immunology," Nat. Rev. Immunol., Feb. 2013, 13(2):88-100.
Walsh et al., "Humanized mouse models of clinical disease," Annu. Rev. Pathol., Jan. 2017, 12:187-215.
Wang et al., "Total body irradiation causes residual bone marrow injury by induction of persistent oxidative stress in murine hematopoietic stem cells," Free Radic. Biol. Med., Jan. 2010, 48(2):348-356.
Wang et al., "The effects of DNA methyltransferase inhibitors and histone deacetylase inhibitors on digit regeneration in mice," Regen. Med., Mar. 2010, 5(2):201-220.

(56) References Cited

OTHER PUBLICATIONS

Willenborg and Eming, "Macrophages-sensors and effectors coordinating skin damage and repair," J. Dtsch Dermatol. Ges., Mar. 2014, 12(3): 214-221.

Wilson et al., "STAT3 is a critical cell-intrinsic regulator of human unconventional T cell numbers and function," J Exp. Med., Jun. 2015, 212(6):855-864.

Winkelmann et al., "Mutations in DNMT1 cause autosomal dominant cerebellar ataxia, deafness and narcolepsy," Hum. Mol. Genet., May 2012, 21(10):2205-2210.

Wojtowicz-Praga, "Reversal of tumor-induced immunosuppression by TGF-beta inhibitors," Invest New Drugs, Feb. 2003, 21(1):21-32.

Wong et al., "Abstract 54: MicroRNA Let-7d-3p in Heart Failure," Circulation Research, Jul. 2016, 119:A54.

Wood et al., "Pro-inflammatory chemokine CCL2 (MCP-1) promotes healing in diabetic wounds by restoring the macrophage response," PLoS One, Mar. 2014, 9(3):e91574, 8 pages.

Yan et al., "Diabetes impairs wound healing by Dnmt1-dependent dysregulation of hematopoietic stem cells differentiation towards macrophages," Nat. Commun., Jan. 2018, 9(1): 33, 13 pages.

Yan et al., "Type 2 diabetes restricts multipotency of mesenchymal stem cells and impairs their capacity to augment postischemic neovascularization in db/db Mice," J. Am. Heart Assoc., Dec. 2012, 1(6):e002238, 16 pages.

Yu et al., "Metabolic regulation by the mitochondrial phosphatase PTPMT1 is required for hematopoietic stem cell differentiation," Cell Stem Cell, Jan. 2013, 12(1):62-74.

Zarin et al., "Gamma delta T-cell differentiation and effector function programming, TCR signal strength, when and how much?," Cell Immunol., Jul. 2015, 296(1):70-75.

Zeisberger et al., "Clodronate-liposome-mediated depletion of tumour-associated macrophages: a new and highly effective antiangiogenic therapy approach," Br. J. Cancer., Aug. 2006, 95(3):272-281.

Zhao et al., "Inflammation in chronic wounds," Int. J. Mol. Sci., Dec. 2016, 17(12). pii:E2085.

Zhu et al., "Developing new chemical tools for DNA methyltransferase 1 (DNMT 1): a small-molecule activity-based probe and novel tetrazole-containing inhibitors," Bioorganic & Med Chemistry, Jun. 2015, 23(12):2917-2927.

Ziegler et al., "Seroconversion to multiple islet autoantibodies and risk of progression to diabetes in children," JAMA, Jul. 2013, 309(23):2473-2479.

Zitvogel et al., "Mechanism of action of conventional and targeted anticancer therapies: reinstating immunosurveillance," Immunity, Jul. 2013, 39(1):74-88.

Zykova et al., "Altered cytokine and nitric oxide secretion in vitro by macrophages from diabetic type II-like db/db mice," Diabetes, Sep. 2000, 49(9):1451-1458.

U.S. Appl. No. 15/004,132, filed Jan. 22, 2016, Louis M. Messina.

Notification of Transmittal of the International Search Report and the Written Opinion of the International Searching Authority for PCT/US 16/14477 dated Apr. 22, 2016, 15 pages.

Rogers et al., "A Role for DNA Hypomethylation and Histone Acetylation in Maintaining Allele-Specific Expression of Mouse NKG2A in Developing and Mature NK Cells," J Immunol 2006, 9 pages.

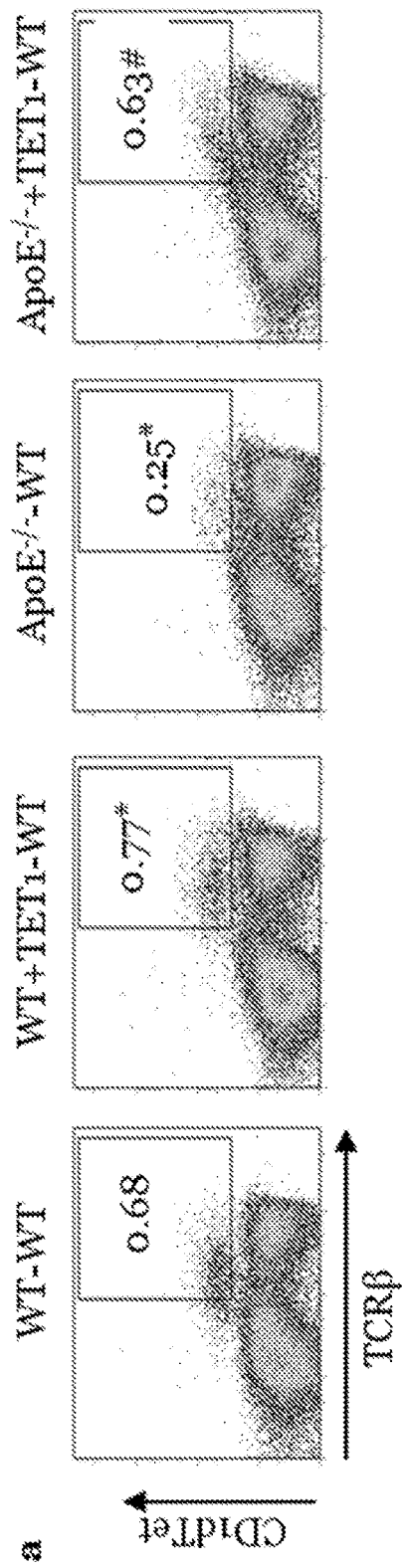
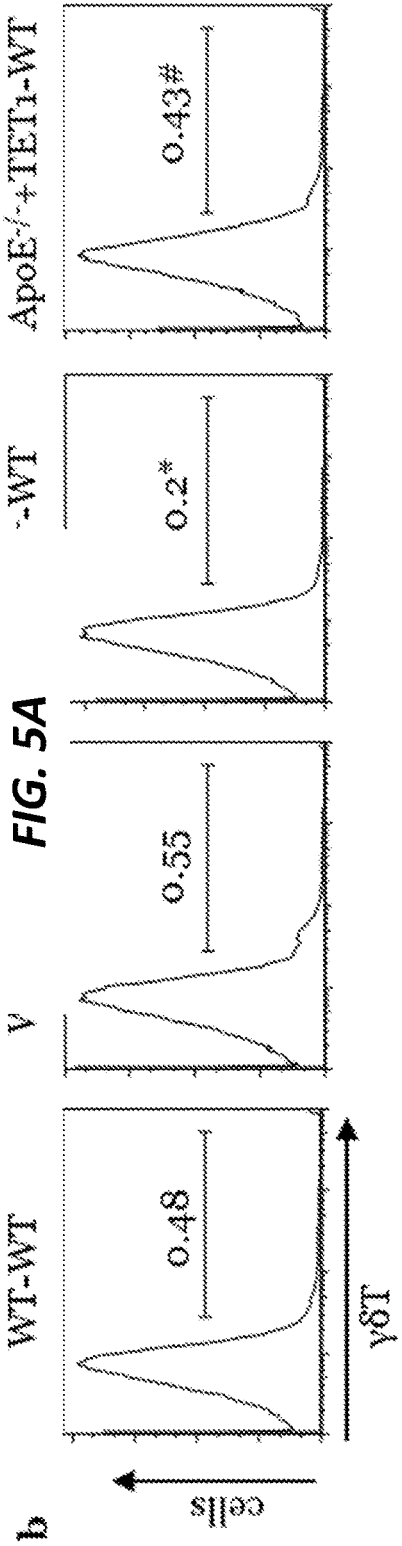
FIG. 5A
FIG. 5B

SEQUENCE LISTING

```
<160> NUMBER OF SEQ ID NOS: 1

<210> SEQ ID NO 1
<211> LENGTH: 2136
<212> TYPE: PRT
<213> ORGANISM: Homo sapiens

<400> SEQUENCE: 1

Met Ser Arg Ser Arg His Ala Arg Pro Ser Arg Leu Val Arg Lys Glu
1               5                   10                  15

Asp Val Asn Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Asp Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
```

```
                210                 215                 220
Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
                260                 265                 270

Leu Gly Ser Arg Val Glu Ser Leu Lys Leu Ser Asp Ser Tyr Leu Asp
                275                 280                 285

Pro Ile Lys Ser Glu His Asp Cys Tyr Pro Thr Ser Ser Leu Asn Lys
                290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
                340                 345                 350

Ala Asn Gln Gln Glu Val Ser Asp Thr Thr Ser Phe Leu Gly Gln Ala
                355                 360                 365

Phe Gly Ala Ile Pro His Gln Trp Glu Leu Pro Gly Ala Asp Pro Val
                370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
                420                 425                 430

Leu Pro Val Pro Pro Asn Pro Ile Ala Thr Phe Asn Ala Pro Ser Lys
                435                 440                 445

Trp Pro Glu Pro Gln Ser Thr Val Ser Tyr Gly Leu Ala Val Gln Gly
                450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
                500                 505                 510

Gln Gly Phe Pro Leu Ala Pro Glu Arg Gly Leu Phe His Ala Ser Leu
                515                 520                 525

Gly Ile Ala Gln Leu Ser Gln Ala Gly Pro Ser Lys Ser Asp Arg Gly
                530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Arg Lys Arg Cys Gly
                580                 585                 590

Val Cys Glu Pro Cys Gln Gln Lys Thr Asn Cys Gly Glu Cys Thr Tyr
                595                 600                 605

Cys Lys Asn Arg Lys Asn Ser His Gln Ile Cys Lys Lys Arg Lys Cys
                610                 615                 620

Glu Glu Leu Lys Lys Lys Pro Ser Val Val Val Pro Leu Glu Val Ile
625                 630                 635                 640
```

```
Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
                660                 665                 670

Asp Tyr Ser Arg Cys Gly His Gly Glu Gln Lys Leu Glu Leu Asn
                675                 680                 685

Pro His Thr Val Glu Asn Val Thr Lys Asn Glu Asp Ser Met Thr Gly
                690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                725                 730                 735

Lys Asn Ser Glu Val Asp Lys Lys Arg Thr Lys Ser Pro Lys Leu Phe
                740                 745                 750

Val Gln Thr Val Arg Asn Gly Ile Lys His Val His Cys Leu Pro Ala
                755                 760                 765

Glu Thr Asn Val Ser Phe Lys Lys Phe Asn Ile Glu Glu Phe Gly Lys
                770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
                805                 810                 815

Lys Gly Arg Ser Asn Val Leu Val Phe Gln Gln Pro Gly Phe Asn Cys
                820                 825                 830

Ser Ser Ile Pro His Ser Ser His Ser Ile Ile Asn His His Ala Ser
                835                 840                 845

Ile His Asn Glu Gly Asp Gln Pro Lys Thr Pro Glu Asn Ile Pro Ser
                850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
                885                 890                 895

Leu Thr Gln Leu Ser Glu Ala Pro Ser Glu Asn Ser Ser Pro Ser Lys
                900                 905                 910

Ser Glu Lys Asp Glu Glu Ser Glu Gln Arg Thr Ala Ser Leu Leu Asn
                915                 920                 925

Ser Cys Lys Ala Ile Leu Tyr Thr Val Arg Lys Asp Leu Gln Asp Pro
                930                 935                 940

Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
                980                 985                 990

Ser His Glu Tyr Ser Lys Val Thr Asn Ser Leu Ser Leu Phe Ile Pro
                995                 1000                1005

Lys Ser Asn Ser Ser Lys Ile Asp Thr Asn Lys Ser Ile Ala Gln Gly
                1010                1015                1020

Ile Ile Thr Leu Asp Asn Cys Ser Asn Asp Leu His Gln Leu Pro Pro
1025                1030                1035                1040

Arg Asn Asn Glu Val Glu Tyr Cys Asn Gln Leu Leu Asp Ser Ser Lys
                1045                1050                1055
```

```
Lys Leu Asp Ser Asp Asp Leu Ser Cys Gln Asp Ala Thr His Thr Gln
            1060                1065                1070

Ile Glu Glu Asp Val Ala Thr Gln Leu Thr Gln Leu Ala Ser Ile Ile
            1075                1080                1085

Lys Ile Asn Tyr Ile Lys Pro Glu Asp Lys Lys Val Glu Ser Thr Pro
            1090                1095                1100

Thr Ser Leu Val Thr Cys Asn Val Gln Gln Lys Tyr Asn Gln Glu Lys
1105                1110                1115                1120

Gly Thr Ile Gln Gln Lys Pro Pro Ser Ser Val His Asn Asn His Gly
                1125                1130                1135

Ser Ser Leu Thr Lys Gln Lys Asn Pro Thr Gln Lys Lys Thr Lys Ser
                1140                1145                1150

Thr Pro Ser Arg Asp Arg Arg Lys Lys Lys Pro Thr Val Val Ser Tyr
                1155                1160                1165

Gln Glu Asn Asp Arg Gln Lys Trp Glu Lys Leu Ser Tyr Met Tyr Gly
                1170                1175                1180

Thr Ile Cys Asp Ile Trp Ile Ala Ser Lys Phe Gln Asn Phe Gly Gln
1185                1190                1195                1200

Phe Cys Pro His Asp Phe Pro Thr Val Phe Gly Lys Ile Ser Ser Ser
                1205                1210                1215

Thr Lys Ile Trp Lys Pro Leu Ala Gln Thr Arg Ser Ile Met Gln Pro
                1220                1225                1230

Lys Thr Val Phe Pro Pro Leu Thr Gln Ile Lys Leu Gln Arg Tyr Pro
                1235                1240                1245

Glu Ser Ala Glu Glu Lys Val Lys Val Glu Pro Leu Asp Ser Leu Ser
                1250                1255                1260

Leu Phe His Leu Lys Thr Glu Ser Asn Gly Lys Ala Phe Thr Asp Lys
1265                1270                1275                1280

Ala Tyr Asn Ser Gln Val Gln Leu Thr Val Asn Ala Asn Gln Lys Ala
                1285                1290                1295

His Pro Leu Thr Gln Pro Ser Ser Pro Asn Gln Cys Ala Asn Val
                1300                1305                1310

Met Ala Gly Asp Asp Gln Ile Arg Phe Gln Gln Val Val Lys Glu Gln
                1315                1320                1325

Leu Met His Gln Arg Leu Pro Thr Leu Pro Gly Ile Ser His Glu Thr
                1330                1335                1340

Pro Leu Pro Glu Ser Ala Leu Thr Leu Arg Asn Val Asn Val Val Cys
1345                1350                1355                1360

Ser Gly Gly Ile Thr Val Val Ser Thr Lys Ser Glu Glu Val Cys
                1365                1370                1375

Ser Ser Ser Phe Gly Thr Ser Glu Phe Ser Thr Val Asp Ser Ala Gln
                1380                1385                1390

Lys Asn Phe Asn Asp Tyr Ala Met Asn Phe Phe Thr Asn Pro Thr Lys
                1395                1400                1405

Asn Leu Val Ser Ile Thr Lys Asp Ser Glu Leu Pro Thr Cys Ser Cys
                1410                1415                1420

Leu Asp Arg Val Ile Gln Lys Asp Lys Gly Pro Tyr Tyr Thr His Leu
1425                1430                1435                1440

Gly Ala Gly Pro Ser Val Ala Ala Val Arg Glu Ile Met Glu Asn Arg
                1445                1450                1455

Tyr Gly Gln Lys Gly Asn Ala Ile Arg Ile Glu Ile Val Val Tyr Thr
                1460                1465                1470

Gly Lys Glu Gly Lys Ser Ser His Gly Cys Pro Ile Ala Lys Trp Val
```

```
                1475                1480                1485
Leu Arg Arg Ser Ser Asp Glu Glu Lys Val Leu Cys Leu Val Arg Gln
            1490                1495                1500
Arg Thr Gly His His Cys Pro Thr Ala Val Met Val Leu Ile Met
1505                1510                1515                1520
Val Trp Asp Gly Ile Pro Leu Pro Met Ala Asp Arg Leu Tyr Thr Glu
            1525                1530                1535
Leu Thr Glu Asn Leu Lys Ser Tyr Asn Gly His Pro Thr Asp Arg Arg
            1540                1545                1550
Cys Thr Leu Asn Glu Asn Arg Thr Cys Thr Cys Gln Gly Ile Asp Pro
            1555                1560                1565
Glu Thr Cys Gly Ala Ser Phe Ser Phe Gly Cys Ser Trp Ser Met Tyr
            1570                1575                1580
Phe Asn Gly Cys Lys Phe Gly Arg Ser Pro Ser Pro Arg Arg Phe Arg
1585                1590                1595                1600
Ile Asp Pro Ser Ser Pro Leu His Glu Lys Asn Leu Glu Asp Asn Leu
            1605                1610                1615
Gln Ser Leu Ala Thr Arg Leu Ala Pro Ile Tyr Lys Gln Tyr Ala Pro
            1620                1625                1630
Val Ala Tyr Gln Asn Gln Val Glu Tyr Glu Asn Val Ala Arg Glu Cys
            1635                1640                1645
Arg Leu Gly Ser Lys Glu Gly Arg Pro Phe Ser Gly Val Thr Ala Cys
            1650                1655                1660
Leu Asp Phe Cys Ala His Pro His Arg Asp Ile His Asn Met Asn Asn
1665                1670                1675                1680
Gly Ser Thr Val Val Cys Thr Leu Thr Arg Glu Asp Asn Arg Ser Leu
            1685                1690                1695
Gly Val Ile Pro Gln Asp Glu Gln Leu His Val Leu Pro Leu Tyr Lys
            1700                1705                1710
Leu Ser Asp Thr Asp Glu Phe Gly Ser Lys Glu Gly Met Glu Ala Lys
            1715                1720                1725
Ile Lys Ser Gly Ala Ile Glu Val Leu Ala Pro Arg Arg Lys Lys Arg
            1730                1735                1740
Thr Cys Phe Thr Gln Pro Val Pro Arg Ser Gly Lys Lys Arg Ala Ala
1745                1750                1755                1760
Met Met Thr Glu Val Leu Ala His Lys Ile Arg Ala Val Glu Lys Lys
            1765                1770                1775
Pro Ile Pro Arg Ile Lys Arg Lys Asn Asn Ser Thr Thr Thr Asn Asn
            1780                1785                1790
Ser Lys Pro Ser Ser Leu Pro Thr Leu Gly Ser Asn Thr Glu Thr Val
            1795                1800                1805
Gln Pro Glu Val Lys Ser Glu Thr Glu Pro His Phe Ile Leu Lys Ser
            1810                1815                1820
Ser Asp Asn Thr Lys Thr Tyr Ser Leu Met Pro Ser Ala Pro His Pro
1825                1830                1835                1840
Val Lys Glu Ala Ser Pro Gly Phe Ser Trp Ser Pro Lys Thr Ala Ser
            1845                1850                1855
Ala Thr Pro Ala Pro Leu Lys Asn Asp Ala Thr Ala Ser Cys Gly Phe
            1860                1865                1870
Ser Glu Arg Ser Ser Thr Pro His Cys Thr Met Pro Ser Gly Arg Leu
            1875                1880                1885
Ser Gly Ala Asn Ala Ala Ala Ala Asp Gly Pro Gly Ile Ser Gln Leu
            1890                1895                1900
```

-continued

```
Gly Glu Val Ala Pro Leu Pro Thr Leu Ser Ala Pro Val Met Glu Pro
1905                1910                1915                1920

Leu Ile Asn Ser Glu Pro Ser Thr Gly Val Thr Glu Pro Leu Thr Pro
                1925                1930                1935

His Gln Pro Asn His Gln Pro Ser Phe Leu Thr Ser Pro Gln Asp Leu
            1940                1945                1950

Ala Ser Ser Pro Met Glu Glu Asp Glu Gln His Ser Glu Ala Asp Glu
            1955                1960                1965

Pro Pro Ser Asp Glu Pro Leu Ser Asp Asp Pro Leu Ser Pro Ala Glu
        1970                1975                1980

Glu Lys Leu Pro His Ile Asp Glu Tyr Trp Ser Asp Ser Glu His Ile
1985                1990                1995                2000

Phe Leu Asp Ala Asn Ile Gly Gly Val Ala Ile Ala Pro Ala His Gly
                2005                2010                2015

Ser Val Leu Ile Glu Cys Ala Arg Arg Glu Leu His Ala Thr Thr Pro
            2020                2025                2030

Val Glu His Pro Asn Arg Asn His Pro Thr Arg Leu Ser Leu Val Phe
            2035                2040                2045

Tyr Gln His Lys Asn Leu Asn Lys Pro Gln His Gly Phe Glu Leu Asn
    2050                2055                2060

Lys Ile Lys Phe Glu Ala Lys Glu Ala Lys Asn Lys Lys Met Lys Ala
2065                2070                2075                2080

Ser Glu Gln Lys Asp Gln Ala Ala Asn Glu Gly Pro Glu Gln Ser Ser
                2085                2090                2095

Glu Val Asn Glu Leu Asn Gln Ile Pro Ser His Lys Ala Leu Thr Leu
            2100                2105                2110

Thr His Asp Asn Val Val Thr Val Ser Pro Tyr Ala Leu Thr His Val
            2115                2120                2125

Ala Gly Pro Tyr Asn His Trp Val
    2130                2135
```

CANCER IMMUNOTHERAPY

CLAIM OF PRIORITY

This application is a national phase application under 35 U.S.C. § 371 of PCT International Application No. PCT/US2016/014477, filed Jan. 22, 2016, which claims the benefit of U.S. Patent Application Ser. No. 62/106,507, filed on Jan. 22, 2015. The entire contents of each of the foregoing applications are hereby incorporated by reference.

TECHNICAL FIELD

The invention relates, at least in part, to methods of providing populations of NKT and/or γδ T cells for use in tumor immunotherapy.

BACKGROUND

Cancer immunotherapies trigger the body's own immune system to find and destroy neoplastic cells. Natural killer T cells (NKT) and γδ T cells have been identified as critical components in cancer immunosurveillance. The initial success of preclinical trials in the last decades has evoked NKT or γδ T cells based immunotherapeutic approaches for the treatment of cancer. However, a significant proportion of patients are not eligible for NKT or γδ T cells based therapies because they don't have either a sufficient number of NKT or γδ T cells and/or lack sufficient cells with normal function. Although stem cell research has found that embryonic stem cells and induced pluripotent stem cells differentiate into NKT and γδ T cells, serving as a potential resource for clinical therapy, their differentiation efficiency is extremely low.

SUMMARY

The present invention is based, at least in part, on the discovery that Tet1 is essential to the differentiation of HSCs toward NKT and/or γδ T cells as well as their function, and that overexpressing Tet1 in hematopoietic stem cells (HSCs) increased their differentiation towards natural killer T cells (NKT) and gamma delta T cells (γδ T cells), e.g., by 10-20 times, in both in vivo and in vitro conditions. In addition, when Tet1 was overexpressed in HSCs they generated not only increased numbers of NKT and γδ T cells, but the cells that were generated were functionally superior in their capacity to kill tumor cells, as injection of WT HSCs that overexpress Tet1 eliminated all of the carcinoma stages of neoplasia.

Thus, in a first aspect the present invention provides methods for preparing a population of Natural Killer T cells (NKT) and/or γδ T cells. The methods include obtaining a first population comprising hematopoietic stem cells (HSC); engineering the HSC to express (i.e., overexpress) Ten eleven translocation (Tet)1; maintaining the Tet1-overexpressing HSC in culture under conditions and for a time sufficient for at least some of the HSC to differentiate into NKT and/or γδ T cells; and optionally purifying the NKT and/or γδ T cells, thereby providing a population of NKT and/or γδ T cells.

Also provided herein is a population of NKT and/or γδ T cells prepared by a method described herein.

In another aspect, the invention provides populations of HSC engineered to overexpress Tet1, e.g., to express exogenous Tet1 or to overexpress endogenous Tet1 to produce levels of Tet1 above those found in normal, non-engineered cells; in some embodiments, the HSCs comprise a Tet1 gene operably linked to a regulatory region other than the endogenous Tet1 regulatory region.

In another aspect, the invention provides methods for treating a subject who has cancer. The methods include administering to the subject a population of NKT and/or γδ T cells described herein, or a population of HSC described herein.

In a further aspect, the invention provides methods for treating a subject who has cancer. The methods include obtaining a first population comprising hematopoietic stem cells (HSC); engineering the HSC to express Ten eleven translocation (Tet)1; and administering the Tet1-overexpressing HSC to the subject, thereby treating the subject.

In yet another aspect, the invention includes methods for treating a subject who has cancer. The methods include obtaining a first population comprising hematopoietic stem cells (HSC); engineering the HSC to overexpress Ten eleven translocation (Tet)1; maintaining the Tet1-expressing HSC in culture under conditions and for a time sufficient for at least some of the HSC to differentiate into NKT and/or γδ T cells; optionally purifying the NKT and/or γδ T cells, and administering the differentiated or purified population of NKT and/or γδ T cells to the subject, thereby treating the subject.

In some embodiments, the first population of HSC is obtained from the subject who has cancer. In some embodiments, the subject has colon cancer, ovarian cancer, prostate cancer, lymphoid malignancies, myeloma, renal cell carcinoma, breast cancer, or malignant glioma, or any cancer sensitive to immunosurveillance.

In an additional aspect, the invention provides methods for increasing levels of NKT and/or γδ T cells in a subject. The methods include obtaining a first population comprising hematopoietic stem cells (HSCs); engineering the HSCs to overexpress Ten eleven translocation (Tet)1; and administering the Tet1-expressing HSC to the subject, thereby increasing levels of NKT and/or γδ T cells in the subject.

In another aspect, the invention provides methods for increasing levels of NKT and/or γδ T cells in a subject. The methods include obtaining a first population comprising hematopoietic stem cells (HSCs); engineering the HSCs to overexpress Ten eleven translocation (Tet)1; maintaining the Tet1-expressing HSC in culture under conditions and for a time sufficient for at least some of the HSC to differentiate into NKT and/or γδ T cells; optionally purifying the NKT and/or γδ T cells, and administering the population of NKT and/or γδ T cells to the subject, thereby increasing levels of NKT and/or γδ T cells in the subject.

In some embodiments, the first population of HSCs is obtained from the subject.

In some embodiments of the methods described herein, the subject has a tumor.

In some embodiments of the methods described herein, the subject has carcinoma, sarcoma, myeloma, leukemia, or lymphoma. In some embodiments of the methods described herein, the subject has colon cancer, ovarian cancer, prostate cancer, lymphoid malignancies, myeloma, renal cell carcinoma, breast cancer, or malignant glioma.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIGS. 5a-f. Reconstitution of lethally irradiated WT mice with ApoE$^{-/-}$ HSCs that overexpresses TET1 restores immunosurveillance against colorectal neoplasia. a, The frequency of NKT cells in thymus and blood of the recipients after transplantation with WT HSCs, ApoE$^{-/-}$ HSCs, TET1-overexpressing WT HSCs+WT HSCs, or TET1-overexpressing ApoE$^{-/-}$ HSCs+ApoE$^{-/-}$ HSCs. n=8, *, p<0.05, vs. WT-WT; #, p<0.05, vs. ApoE$^{-/-}$-WT. b. The frequency of γδ T cells in thymus and blood of the recipients. n=8, *, p<0.05, vs. WT-WT; #, p<0.05, vs. ApoE$^{-/-}$-WT. c, The frequency of NKT cells in colon of the recipients. n=8, , p<0.01, vs. WT-WT; #, p<0.05, vs. ApoE$^{-/-}$-WT. d, The frequency of γδ T cells in colon of the recipients. n=8, , p<0.01, vs. WT-WT; #, p<0.05, vs. ApoE$^{-/-}$-WT. e, Average tumor numbers per mouse in the recipients. n=12, *, p<0.05, vs. WT-WT; #, p<0.05, vs. ApoE$^{-/-}$-WT. f, Histopathologic stages of tumors. n=12, *, p<0.05, **, p<0.01 vs. WT-WT; #, p<0.05, ##, p<0.01, vs. ApoE$^{-/-}$-WT.

DETAILED DESCRIPTION

Figure 1A:
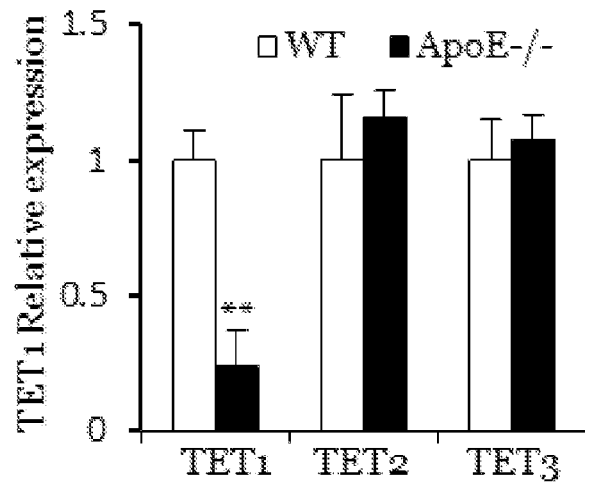
FIGS. 1a-j. Hypercholesterolemia induced oxidant stress downregulates the expression of TET1 in HSCs that impairs their differentiation towards NKT and γδ T cells. a, The expression of TET1, TET2 and TET3 in HSCs from WT and ApoE$^{-/-}$ mice. n=6, **, p<0.01, vs. WT. b, Oxidant stress dependent downregulation of TET1 expression in HSCs from ApoE$^{-/-}$ mice. n=6, *<0.05; **, p<0.01, vs. ApoE$^{-/-}$. c, The deletion of TET1 in HSCs. n=6, *, p<0.05; **, p<0.01, vs. WT; #, p<0.05, vs. ApoE$^{-/-}$. d, The differentiation of HSCs towards NKT in vitro. n=6, *, p<0.05; **, p<0.01, vs. WT; #, p<0.05, vs. ApoE$^{-/-}$. e. The differentiation of HSCs towards γδ T cells in vitro. n=6, *, p<0.05; **, p<0.01, vs. WT; #, p<0.05, vs. ApoE$^{-/-}$. f, The overexpression of TET1 in HSCs. n=6, *, p<0.05; **, p<0.01, vs. WT; #, p<0.05; ##, p<0.01, vs. ApoE$^{-/-}$. g, The differentiation of HSCs towards NKT in vitro. n=6, *, p<0.05; **, p<0.01, vs. WT; #, p<0.05, vs. ApoE$^{-/-}$. h. The differentiation of HSCs towards γδT cells in vitro. n=6, *, p<0.05; **, p<0.01, vs. WT; #, p<0.05, vs. ApoE$^{-/-}$. i, The differentiation of HSCs towards NKT cells in vivo. n=6, *, p<0.05; **, p<0.01, vs. WT; #, p<0.05, vs. ApoE$^{-/-}$. j. The differentiation of HSCs towards γδT cells in vivo. n=6, *, p<0.05; **, p<0.01, vs. WT; #, p<0.05, vs. ApoE$^{-/-}$.

Natural killer T (NKT) cells, defined by the expression of both αβ T-cell receptors (TCR) and lineage markers of natural killer (NK) cells, are a small population of lymphocytes that possess characteristics of both innate and adaptive immune cells (1,2). Upon activation, NKT and γδT cells rapidly secrete a variety of cytokines, including interferon γ (IFNγ), interleukins (IL)-4, IL-13, IL-17, tumor necrosis factor α (TNFα), and granulocyte macrophage colony-stimulating factor (GM-CSF) (Hayday, Annu Rev Immunol. 18, 975-1026 (2000); Brennan et al., Nat Rev Immunol. 13, 101-17 (2013)). Along with the mediators produced by antigen-presenting cells with which NKT and γδT cells interact, these cytokines recruit and stimulate the anti-tumor functions of cytotoxic lymphocytes, boosting innate as well as adaptive antitumor responses. Activated NKT and γδT cells both have strong cytotoxic effector activity (Chien et al., Annu Rev Immunol. 32, 121-55 (2014); Taniguchi et al., Nat Immunol. 4, 1165-1165 (2003); Todaro et al., J Immunol. 182, 7287-7296 (2009)). In this context, NKT and γδT cells function as major participants in tumor immunosurveillance. Recent studies showed that iNKT-deficient mice exhibited significantly increased susceptibility to methyl-cholanthrene-(MCA) induced sarcomas and B16F10 melanoma tumors (3), an effect reversed by the administration of liver-derived iNKT cells during the early stages of tumor growth (4). Interferon (IFN)-γ production by NKT cells has also been shown to be critical in tumor rejection. The primary contribution of NKT cells to tumor immunosurveillance occurs indirectly via the activation of NKT cells by dendritic cells (DC) presenting alpha-galactosylceramide (α-GalCer). Activated NKT cells then initiate a series of cytokine cascades that help boost the priming phase of the antitumor immune response. These studies indicate that NKT cells are an essential component in the immunosurveillance against cancers.

T lymphocytes bearing γ- and δ-chain T-cell receptor heterodimers are named γδ T cells and have been identified as another important cellular component in the immunosurveillance against cancer. Antigen recognition of γδ T-cell receptors is very unique, and the responses frequently exhibit innate characteristics. Furthermore, peripheral γδ T cells exert a number of effector and regulatory functions (5). γδ T cells rapidly produce cytokines like IFN-γ and IL-17 and promote inflammation, partly due to their inherent epigenetic and transcriptional programs, which facilitates a rapid and comprehensive killing response to neoplastic cells. Moreover, γδ T cells lyse target cells directly, which is necessary for pathogen or tumor clearance (6).

Recent studies have shown that NKT and γδ T cells could be steadily expanded in vitro and employed in cancer immunotherapy. Clinical trials have been completed in a cohort of 17 patients with advanced non-small cell lung cancers and 10 cases of head and neck tumors. Sixty percent of advanced lung cancer patients with high IFN-γ production had significantly prolonged median survival times of 29.3 months with only the primary treatment. In the case of head and neck tumors, 10 patients who completed the trial all had stable disease or partial responses five weeks after the combination therapy of α-GalCer-DCs and activated NKT cells. Cancer immunotherapy trials with autologous γδ T cells have been investigated in parallel by Japanese, Australian and French groups. Their results suggested that γδ T cells based therapy is well tolerated and therapeutically effective, as many patients showed stabilized diseases following this treatment (7, 8, 9, 10).

Based on the initial success in preclinical trials, intense efforts have been made in the last decades to launch NKT or γδ T cells based immunotherapeutic approaches for the treatment of cancer. However, a significant proportion of patients are not eligible for NKT or γδ T cells based therapies because they don't have sufficient NKT and/or γδ T cells (11, 12). Although stem cell research has provided evidence that embryonic stem cells and induced pluripotent stem cells differentiated into NKT and γδ T cells in vitro, serving as a potential resource for clinical therapy, the differentiation efficiency is questionable (12,13). Therefore, it is a priority goal in NKT or γδ T cell based cancer immunotherapy to establish an adequate and reliable resource of these cells.

Enhancing Hematopoietic Stem Cell Differentiation toward NKT and γδ T Cells

Described herein are methods for creating populations of NKT and γδ T cells by overexpressing Ten eleven translocation (Tet)1 in hematopoietic stem cells. Members of the Tet protein family, including Tet1, Tet2 and Tet3, are ketoglutarate and Fe2+ dependent enzymes that can specifically modify DNA by demethylation (14,15,16). Within the Tet family, Tet2 has been shown to have a critical role in regulating the self-renewal, proliferation and differentiation of HSCs (14, 17), whereas the role of Tet1 in hematopoiesis was previously unknown. The present inventors found that Tet1-dependent epigenetic regulation is a novel determinant in the differentiation of hematopoietic stem cells (HSCs) towards NKT and γδT cells. Tet1 overexpression in HSCs dramatically increases the differentiation of HSCs towards NKT and γδT cells and restores the impaired immunosurveillance against colorectal cancer in hypercholesterolemic mice. Based on these findings, the present methods can be used to provide human NKT and γδ T cells for cancer immunotherapy by manipulating Tet1 dependent epigenetic regulation in HSCs.

Thus, the present methods include obtaining a first population of hematopoietic stem cells (HSC), preferably from an affected person. Preferably, the HSCs are obtained from a human subject who is going to receive the immunotherapy treatment with NKT and γδ T cells, i.e., the cells are autologous; alternatively, they can be allogeneic. Methods for obtaining enriched populations of HSC are known in the art and include cell sorting based on expression of one or more cell surface markers; in some embodiments, the HSC used in the present methods are CD34+; in some embodiments, the cells are CD34+, Thy-1+; in some embodiments, the cells are CD34+, CD59+, Thy1/CD90+, CD38lo/−, C-kit/CD117+, and/or lin−. For example, primary human CD34+-enriched cells can be obtained from peripheral blood, e.g., after treatment of the donor with a mobilizing cytokine such as granulocyte-colony stimulating factor (GCSF). Other sources of HSC include bone marrow and umbilical cord blood. A number of methods are known in the art for preparing enriched populations of HSC, e.g., as described in Rector et al., Methods Mol Biol. 2013; 976:1-15. For example, the cells can be sorted, e.g., using columns (e.g., the MiniMACS LS+ separation columns (Miltenyi Biotec, Auburn, Calif.)), e.g., using commercially available kits, e.g., the CD34-progenitor cell isolation kit (StemCell Technologies, Vancouver, BC, Canada), according to the manufacturer's protocol. A population of cells that is enriched for HSCs is at least 20% HSC, e.g., is at least 30%, 40%, 50%, 60%, 70%, 80%, 90%, or 95% HSCs. In some embodiments, the HSCs used in the present methods are obtained by enriching for cells that are CD34+; in some embodiments, the cells are obtained by enriching for cells that are CD34+, Thy-1+; in some embodiments, the cells are obtained by enriching for cells that are CD34+, CD59+, Thy1/CD90+, CD38lo/−, C-kit/CD117+, lin−.

Tet1

The enriched populations of HSCs used in the present methods and compositions are engineered to express the Tet1 protein. The sequence of human Tet1 is as follows:

```
                                                          (SEQ ID NO: 1)
    1    msrsrharps  rlvrkedvnk  kkknsqlrkt  tkganknvas  vktlspgklk  gligerdvkk 61    ktepkppvpv  rslltragaa  rmnldrtevl  fqnpesltcn  gftmalrsts  lsrrlsqppl 121    vvakskkvpl  skglekqhdc  dykilpalgv  khsendsvpm  qdtqvlpdie  tligvqnpsl 181    lkgksgettq  fwsqrvedsk  inipthsgpa  aeilpgpleg  trcgeglfse  etlndtsgsp 241    kmfaqdtvca  pfpqratpkv  tsqgnpsiql  eelgsrvesl  klsdsyldpi  ksehdcypts 301    slnkvipdln  lrnclalggs  tsptsvikfl  lagskqatlg  akpdhqeafe  atanqqevsd 361    ttsflgqafg  aiphqwelpg  adpvhgealg  etpdlpeipg  aipvqgevfg  tildqqetlg 421    msgsvvpdlp  vflpvppnpi  atfnapskwp  epqstvsygl  avqgaigilp  lgsghtpqss 481    snseknslpp  vmaisnvene  kqvhisflpa  ntqgfplape  rglfhaslgi  aqlsqagpsk 541    sdrgssqvsv  tstvhvvntt  vvtmpvpmvs  tssssyttll  ptlekkkrkr  cgvcepcqqk 601    tncgectyck  nrknshqick  krkceelkkk  psvvvplevi  kenkrpqrek  kpkvlkadfd 661    nkpvngpkse  smdysrcghg  eeqklelnph  tvenvtkned  smtgievekw  tqnkksqltd 721    hvkgdfsanv  peaeksknse  vdkkrtkspk  lfvqtvrngi  khvhclpaet  nvsfkkfnie
```

-continued

```
 781    efgktlenns ykflkdtanh knamssvatd mscdhlkgrs nvlvfqqpgf ncssiphssh 841    siinhhasih negdqpktpe nipskepkdg spvqpsllsl mkdrrltleq vvaiealtql 901    seapsenssp sksekdeese qrtasllnsc kailytvrkd lqdpnlqgep pklnhcpsle 961    kqsscntvvf ngqtttlsns hinsatnqas tksheyskvt nslslfipks nsskidtnks 1021    iaqgiitldn csndlhqlpp rnneveycnq lldsskklds ddlscqdath tqieedvatq 1081    ltqlasiiki nyikpedkkv estptslvtc nvqqkynqek gtiqqkppss vhnnhgsslt 1141    kqknptqkkt kstpsrdrrk kkptvvsyqe ndrqkwekls ymygticdiw iaskfqnfgq 1201    fcphdfptvf gkissstkiw kplaqtrsim qpktvfpplt qiklqrypes aeekvkvepl 1261    dslslfhlkt esngkaftdk aynsqvqltv nanqkahplt qpssppnqca nvmagddqir 1321    fqqvvkeqlm hqrlptlpgi shetplpesa ltlrnvnvvc sggitvvstk seeevcsssf 1381    gtsefstvds aqknfndyam nfftnptknl vsitkdselp tcscldrviq kdkgpyythl 1441    gagpsvaavr eimenrygqk gnairieivv ytgkegkssh gcpiakwvlr rssdeekvlc 1501    lvrqrtghhc ptavmvvlim vwdgiplpma drlytelten lksynghptd rrctlnenrt 1561    ctcqgidpet cgasfsfgcs wsmyfngckf grspsprrfr idpssplhek nledn1qsla 1621    trlapiykqy apvayqnqve yenvarecrl gskegrpfsg vtacldfcah phrdihnmnn 1681    gstvvctltr ednrslgvip qdeqlhvlpl yklsdtdefg skegmeakik sgaievlapr 1741    rkkrtcftqp vprsgkkraa mmtevlahki ravekkpipr ikrknnsttt nnskpsslpt 1801    lgsntetvqp evksetephf ilkssdntkt yslmpsaphp vkeaspgfsw spktasatpa 1861    plkndatasc gfsersstph ctmpsgrlsg anaaaadgpg isqlgevapl ptlsapvmep 1921    linsepstgv tepltphqpn hqpsfltspq dlasspmeed eqhseadepp sdeplsddpl 1981    spaeeklphi deywsdsehi fldaniggva iapahgsvli ecarrelhat tpvehpnrnh 2041    ptrlslvfyq hknlnkpqhg felnkikfea keaknkkmka seqkdqaane gpeqssevne 2101    lnqipshkal tlthdnvvtv spyalthvag pynhwv
```

In some embodiments, the Tet1 proteins that are expressed in the enriched HSCs can be at least about 80%, 85%, 90%, 95%, 98% or more homologous to SEQ ID NO:1, and maintain the ability to promote HSC differentiation to NKT or γδ T cells. In some embodiments the Tet1 comprises the catalytic domain of Tet1, e.g., amino acids 1418-2136 of SEQ ID NO:1, or a sequence that is at least about 80%, 85%, 90%, 95%, 98% or more homologous to amino acids 1418-2136 of SEQ ID NO:1 and maintains the ability to promote HSC differentiation to NKT or γδ T cell. Another exemplary nucleic acid sequence encoding human Tet1 is in GenBank at Acc. No. NM_030625.2.

Recombinant Expression Vectors, Host Cells and Genetically Engineered Cells

Generally speaking, the HSC are engineered to express Tet1 by transduction with a nucleic acid, e.g., expression vectors, containing a nucleic acid encoding a Tet1 polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the gene construct or CaPO4 precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors can provide effective delivery of genes into cells. Whereas the transgene within a retroviral vector is typically stably integrated into the chromosomal DNA of the host, the transgene of an AAV vector usually exists as extrachromosomal episomes within the cytoplasm of infected cells. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of to its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993).

Typically, an expression vector includes the nucleic acid in a form suitable for expression of the human Tet1 in an HSC. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the level of expression of protein desired and whether regulated or inducible expression is desired. The expression vectors can be introduced into HSCs. The expression vector is preferably a vector suitable for expression in mammalian cells, and the expression vector's control functions can be provided by viral regulatory elements. For example, commonly used promoters are derived from polyoma, Adenovirus 2, cytomegalovirus and Simian Virus 40. See, e.g., Wang et al., Exp Hematol. 2008 July; 36(7):823-31.

In another aspect the invention provides HSC that include and optionally express a Tet1 nucleic acid molecule described herein, e.g., a Tet1 nucleic acid molecule within a recombinant expression vector or a Tet1 nucleic acid molecule containing sequences which allow it to homologously recombine into a specific site of the HSC's genome. The term HSC refers not only to the particular subject cell that is transduced but to the progeny or potential progeny of such a cell that contain the Tet1 nucleic acid. Because certain modifications may occur in succeeding generations due to either mutation or environmental influences, such progeny may not, in fact, be identical to the parent cell, but are still included within the scope of the term as used herein.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

In another aspect, the invention features an HSC cell or purified preparation of HSCs that include a Tet1 transgene, which over-express Tet1 or express Tet1 in response to a stimulus.

Also provided herein are human hematopoietic stem cells, in which an endogenous Tet1 is under the control of an exogenous regulatory sequence that does not normally control the expression of the endogenous Tet1 gene, and that express Tet1 under circumstances in which a cell that lacks the exogenous regulatory sequence do not express Tet1. The expression characteristics of an endogenous Tet1 gene within a cell can be modified by inserting a heterologous DNA regulatory element into the genome of the cell such that the inserted regulatory element is operably linked to the endogenous Tet1 gene. For example, an endogenous Tet1 gene that is "transcriptionally silent," e.g., not normally expressed, or expressed only at very low levels, may be activated by inserting a regulatory element capable of promoting the expression of a normally expressed gene product in that cell. Techniques such as targeted homologous recombination can be used to insert the heterologous DNA as described in, e.g., Chappel, U.S. Pat. No. 5,272,071; WO 91/06667, published in May 16, 1991.

The methods can also include identifying, selecting, and/or purifying those cells that overexpress Tet1, or that express Tet1 over a desired level.

The Tet1-expressing cells can be used for administration to a subject, can be frozen or otherwise stored for later administration to a subject, or can be maintained under conditions such that the HSC differentiate into NKT and γδ T cells. These conditions can include those previously described. For example, c-kit+Sca-1+Lin− (KSL) hematopoietic stem cells can be seeded, e.g., at $4 \times 10^3$ cells/well into 12-well tissue culture plates, containing a confluent monolayer of OP9-DL1 cells; see, e.g., Holmes and Zuniga-Pflucker, Cold Spring Harb Protoc 2009: oi:10.1101/pdb.prot5156 (2009)). In some embodiments, the cultures are performed in the presence of one or more cytokines or growth factors, e.g., 5 ng/mL IL-2, 10 ng/mL GM-CSF (Stem cell Technology), 5 ng/mL, IL-7, and 5 ng/mL mFLT3 (Peprotech).

NKT cells can be identified by methods known in the art, e.g., by the presence of TCRαβ and NK1.1 or CD1d-tet (see, e.g. Godfrey et al., Nature Reviews Immunology 4, 231-237 (2004)); γδ T cells can be identified by methods known in the art, e.g., by the presence of γδ TCR (see, e.g., Holtmeier and Kabelitz, Chemical Immunology and Allergy 86: 151-83 (2005)). The cells can be maintained in culture until a desired number of cells, e.g., of HSC or NKT and γδ T cells, is obtained, and then harvested for use or freezing. The methods can also include purifying the NKT and/or γδ T cells away from the Tet1-expressing HSC, to provide purified populations of NKT and/or γδ T cells.

Methods of Targeting Neoplasias

The present methods include the use of enriched populations of Tet1-expressing HSC, or NKT and γδ T cells obtained from Tet1-expressing HSC, for treating a neoplasia, e.g., a tumor, in a subject. As noted in Bennouna et al., Cancer Immunol Immunother (2010) 59:1521-1530, "An expansive body of literature in the field has documented that cd T cells, which represent 1-10% of human peripheral T cells, kill solid and hematologic tumors originating from virtually any organ type." NKT and γδ T cells have been shown to be effective in treating a wide range of lymphoid malignancies as well as solid tumor-associated cancers, including colon cancer, colorectal cancer; gastrointestinal carcinoma, hepatocarcinoma, esophageal cancer, ovarian cancer, prostate cancer, myeloma, renal cell carcinoma, breast cancer, non-small cell lung cancer, and malignant glioma, among others, see, e.g., Fisher et al., Oncoimmunology. 2014; 3: e27572; Kobayashi et al., Anticancer Research 31: 1027-1032 (2011); Motohashi et al., Clin Cancer Res 2006; 12:6079-6086; Bennouna et al., Cancer Immunol Immunother (2010) 59:1521-1530; and Kobayashi et al., Cancer Immunol Immunother (2007) 56:469-476.

Thus the present methods can include identifying a subject who has a neoplasm, e.g., a tumor, and administering to the subject a therapeutically effective amount of a population of Tet1-expressing HSC, or NKT and/or γδ T cells obtained from Tet1-expressing HSC. In some embodiments, the Tet1-expressing HSC, NKT and/or γδ T cells are prepared by a method described herein from a population of the subject's own (autologous) HSC; in some embodiments, the HSC are obtained from a related or unrelated type-matched donor. In some embodiments, the neoplasm is a tumor, e.g., a tumor that is sensitive to innate immunity against cancer or immunosurveillance, e.g., carcinoma, sarcoma, myeloma, leukemia, or lymphoma. In some embodiments, the methods include determining a level of native NKT and/or γδ T cells in the subject, comparing the level of NKT and/or γδ T cells to a reference level (e.g., a level of NKT and/or γδ T cells determined, based on analysis of a cohort of subjects, to correlate to a level of NKT and/or γδ T cells in subjects who would benefit from the administration of additional NKT and/or γδ T cells, e.g., subjects who are deficient in native NKT and/or γδ T cells). The levels of NKT and/or γδ T cells can be measured, e.g., in the circulating blood, in the thymus, and/or in a tumor in the subject.

EXAMPLES

The invention is further described in the following examples, which do not limit the scope of the invention described in the claims.

Materials and Methods

The following materials and methods were used in the examples set forth herein.

Mice

All mice were purchased from Jackson Laboratories (Bar Harbor, Me.) and were maintained in the mouse barrier facility. Care of mice was in accordance with NIH guidelines and the Institutional Animal Care and Use Committee of the University of Massachusetts Medical School approved all protocols. Mice were kept on a 12 hr day/night schedule and were allowed free access to chow and water. ApoE$^{-/-}$ and WT mice were fed standard mouse chow (5.4 g fat/100 g diet, 0% cholesterol). HCD mice were fed a diet with 10 g fat/100 g diet, 11.25 g cholesterol/100 g diet (Research Diets, New Brunswick, N.J.). NAC was given for 8 weeks (150 mg/kg/day via drinking water).

Tumor Induction and Analysis

The colorectal neoplasia were performed as described in previous publications (Greten et al., Cell. 118(3), 285-96 (2004)). Three month old mice were subcutaneously injected with a solution of Azoxymethane (AOM) at a dose rate of 15 mg/kg body weight, once weekly for 3 successive weeks. 2% DSS was given in the drinking water over five days in the last week. Mice were sacrificed ten weeks after the last injection of AOM. Colons were removed and flushed with PBS. Sections (5 μm) were cut stepwise (200 μm) through the complete block and stained with H&E. Tumors counts were performed in a blinded fashion. To determine the histopathologic stages of tumors, the sections of tumors were read by cancer pathologists in a blind fashion.

Flow Cytometry

Cells were stained with monoclonal antibodies conjugated to various fluoroprobes. These antibodies included: cKit (2B8), Sca-1 (E13-161.7), CD4 (L3T4), CD8 (53-6.72), CD90.1, CD25, CD44, TCRβ, NK1.1, γδTCR, CD45.1, CD45.2. The lineage cocktail consisted of CD4, CD8, B220 (RA3-6B2), TER-119, Mac-1 (MI/70), and Gr-1 (RB6-8C5). All antibodies were purchased from BD Bioscience (San Diego, Calif.). CD1d-aGalCer tetramer was obtained from the NIH Tetramer facility. FACS analysis was carried out on a FACS Diva or MoFlow.

Lentiviral Particle Preparation and Transduction

The Tet1 specific and control shRNA plasmids were both purchased from Santa Cruz (Calif., USA). The plasmid with TET1 catalytic domain (pTYF-U6-shCONT-EF1-Puro-2A-CD1) was a gift from Dr Yi Zhang (Massachusetts General Hospital, Boston, Ma.). The envelope and helper plasmids were purchased from ABM (Toronto, Canada). The lentiviral particles were prepared according to the kit instruction. The lentivirus-containing supernatant was harvested 2 days post-transfection. Fresh isolated KSL cells were transduced with lentivirus for 24 hours and then selected with puromycin (2 μg/ml) (Santa Cruz Biotechnology, Calif., USA) for 72 hours.

HSCs and OP9 Cell Co-Culture

The co-culture was performed as described (e.g., Holmes and Zuniga-Pflucker, Cold Spring Harb Protoc 2009: oi:10.1101/pdb.prot5156 (2009)). KSL cells were seeded at $4\times10^3$ cells/well into 12-well tissue culture plates containing a confluent monolayer of OP9-DL1 cells. OP9-DL1 cells were a kind gift from Dr. Juan Carlos Zuniga-Pflucker (University of Toronto). All cultures were performed in the presence of 5 ng/mL IL-2, 10 ng/mL GM-CSF (Stem cell Technology), 5 ng/mL, IL-7, 5 ng/mL mFLT3 (Peprotech). Co-cultures were harvested by forceful pipetting at the indicated time points.

Immunohistochemistry

We used a standard protocol to detect NKT and γδ T cells in colon and tumor tissues. The antibodies were purchased from BD Biosciences (MA, USA). For indirect immunohistochemistry, we used rabbit-specific IgG conjugated with FITC or PE (Chemicon) as a secondary antibody. For nuclear staining, we treated specimens with DAPI (Molecular Probes). Fluorescent images were obtained using a confocal laser scanning microscope (Carl Zeiss LSM 510 system; Carl Zeiss).

Analysis of Intracellular ROS

We loaded samples of cultures with DCF-DA (Sigma) and incubated them on a shaker at 37° C. for 30 min. The peak excitation wavelength for oxidized DCF was 488 nm, and emission was 525 nm. The concentration of H2O2 was measured by Amplex Red Hydrogen Peroxide/Peroxidase Assay Kit (Molecular Probes).

Chromatin Immunoprecipitation (ChIP)

ChIP was performed with minor modifications of the procedure described by Yildirim et al. (Nature Structural & Molecular Biology 19:56-61 (2012)). Approximately $6\times10^6$ Hepa-1 cells were incubated for 10 min at room temperature with 1% formaldehyde. After cross-linking, the reaction was quenched with 0.25 M glycine for 10 min at room temperature. Proteins are initially cross-linked to DNA and nuclei are pelleted and sonicated to 200-500 bp fragments (Bioruptor, Diagenode). The cross-linked DNA was immunoprecipitated with H3K4me3 or H3K27me3 antibodies (Millipore, USA) overnight at 4° C. with rotation, DNA-Antibody complexes were bound to ChIP beads, pulled down, washed and then eluted from beads. Following reversal of cross-linkage purified DNA was used for Quantitative PCR using ChIP PCR primers which were purchased from IDT (MA, USA). Immunoprecipitation efficiency was calculated by normalizing sample $C_T$ values against control IgG values and calculating ratios of sample $C_T$ values relative to input values.

RTPCR and qRT-PCR Array

We reverse transcribed cDNAs from total RNA isolated from each cell fraction using Trizol LS (Invitrogen). Transcription to cDNA was performed using SuperScript III (Invitrogen). All PCRs were carried out in triplicate using an Eppendorf Mastercycler (Eppendorf).

DNA Extraction, Bisulfite Conversion and Pyrosequencing

Genomic DNA was extracted from freshly isolated cells using QIAamp DNA MiniKit (Qiagen Inc., Hilden, Germany) and quantified by UV absorption. 200-300 ng of DNA was used in the bisulfite conversion reactions where unmethylated cytosines were converted to uracil with the Epi-Tect Bisulfite kit (Qiagen) according to manufacturer's instructions. Briefly, DNA was mixed with water, DNA protect buffer and bisulfite mix and the conversion was run in a thermocycler (Biometra, Goettingen, Germany) at the recommended cycle conditions. Converted DNA was purified on a spin column and eluted twice into a total of 40 μl Buffer EB.

PCR and Pyrosequencing

Primer sets with one biotin-labelled primer were used to amplify the bisulfite converted DNA. New primers for each gene were designed using PyroMark Assay Design software version 2.0.1.15 (Qiagen). The size of the amplicons was restricted to a maximum of 210 bp. Due care was taken to avoid any primer overlapping CG dyads to prevent amplification biases.

We examined at least two different sites within the CpG islands separated by several hundred base pairs. To provide the internal control for total bisulfite conversion, a non-CG cytosine in the region for pyrosequencing was included where possible. PCRs were performed using a converted DNA equivalent of 200 cells employing the PyroMark PCR kit (Qiagen). The cell genome-equivalents of DNA calculations assumed 6 pg DNA per diploid cell. Briefly, 12.5 μl master mix, 2.5 μl Coral red, 5 pmol of each primer, 7 μl of water and 2 μl sample were mixed for each reaction and run at thermal cycling conditions: 95° C. for 15 min and then 45 cycles: 30 sec at 94° C.; 30 sec at the optimized primer-specific annealing temperature; 30 sec at 72° C. and a final extension for 10 min at 72° C. The amplified DNA was confirmed by electrophoresis in a 2% low melting point agarose gel (Sigma-Aldrich, Steinheim, Germany). 3 μl streptavidin beads (GE Healthcare, Buckinghamshire, UK), 37 μl PyroMark binding buffer (Qiagen), 20 μl PCR product and 20 μl water were mixed and incubated for 10 min on a shaking table at 1300 rpm. Using the Biotage Q96 Vaccum Workstation, amplicons were separated, denatured, washed and added to 45 μl annealing buffer containing 0.33 μM of pyrosequencing primer. Primer annealing was performed by incubating the samples at 800° C. for 2 min and allowed to cool to room temperature prior to pyrosequencing. PyroGold reagents were used for the pyrosequencing reaction and the signal was analyzed using the PSQ 96MA system (Biotage, Uppsala, Sweden). Target CGs were evaluated by instrument software (PSQ96MA 2.1) which converts the pyrograms to numerical values for peak heights and calculates proportion of methylation at each base as a C/T ratio. All runs contained standard curves, which comprised a range of control methylated DNA (0%, 25%, 50%, 75%, and 100%) to allow standardized direct comparisons between different primer sets. For the standard curves a total of 300 ng of unmethylated (Qiagen) and hypermethylated DNA (Millipore, Billerica, Ma., USA) were mixed to obtain the different ratios of DNA methylation and then bisulfite converted as described above.

In Vitro Differentiation of Human Bone Marrow Derived HSCs

Human bone marrow-derived HSCs were isolated and differentiated in vitro as follows.

1. Isolation of Human Hematopoietic Stem Cells from Bone Marrow Aspirate

Fresh bone marrow aspirate is obtained from donors. Bone fragments and cells are filtered through 40-μm cell strainer. Mononuclear cells from bone marrow aspirate are separated with histopaque-1077 (Sigma, 3000 rpm, 30 min, room temperature). CD34+Lineage− (CD4, CD8, CD11b, CD19, CD45R, CD161, GR.1, Ter119) progenitor cells or HSCs are isolated with flow cytometric cell sorting. If required, HSCs will be transfected with Lenti-Tet1 and selected by puromycin (5 μg/ml). 5×103 cells (normal HSCs, or Tet1-overexpressing HSCs) are seeded in 10 mL of OP9 medium per 10-cm dish of 80%-90% confluent OP9 or OP9-DL1 cells. Add 5 ng/mL Flt-3L, 5 ng/mL IL-3 and 1 ng/mL IL-7 for γδT cell differentiation. Add 5 ng/mL GM-CSF, 5 ng/mL IL-3 and 2 ng/mL IL-2 for NKT cell differentiation.

2. In Vitro Differentiation 5 days later, disaggregate cells without the use of trypsin by pipetting the cells up and down until the OP9 cell monolayer is completely disrupted from the plate and broken into small pieces. Filter cells through a 40-μm cell strainer. Wash the 10-cm dish with 6 mL of PBS, filter through the same cell strainer, and centrifuge at 400 g (1500 rpm) for 5 min at 4° C. Resuspend the cells in 10 mL of OP9 medium (alpha MEM supplied with 20% FBS, 1% antibiotics) containing cytokines, and seed the cells onto 10-cm dishes of 80%-90% confluent fresh OP9 or OP9-DL1 cells. Measure NKT or γδT cell populations by FSCS 6 weeks after coculture.

3. IL-3 Supplement

We bought bone marrow aspirate from All Cell Co Ltd. The samples were collected and delivered to our lab by overnight shipment on ice. We found that some HSCs isolated from the samples did not grow very well. To overcome the problem, we supplied 5 ng/mL IL-3 in HSC culture medium. In the last culture, IL-3 supplement enhanced the proliferation of human HSCs. This observation is supported by previous studies (Bryder et al, Blood, 2000, 96, 1748). We did not have any evidence to show IL-3 supplement affects the differentiation of HSCs towards T lineages yet.

Statistical Analysis

All data were shown as means±sd. Statistical analyses were carried out with either GraphPad Prism (GraphPad Software) or SPSS v19 (IBM) software. Statistical significance was evaluated by using a one- or two-way analysis of variance (ANOVA) or an unpaired t-test. Significance was established for P values of at least <0.05.

Example 1. Hypercholesterolemia Downregulates the Expression of Tet1 in HSCs Which Functions as Pivotal Regulator in the Differentiation from HSCs Towards NKT and γδ T Cells Hypercholesterolemia (HC) increases the incidence and histopathologic severity of colorectal neoplasia by an HSC-autonomous mechanism.

Figure 1B:
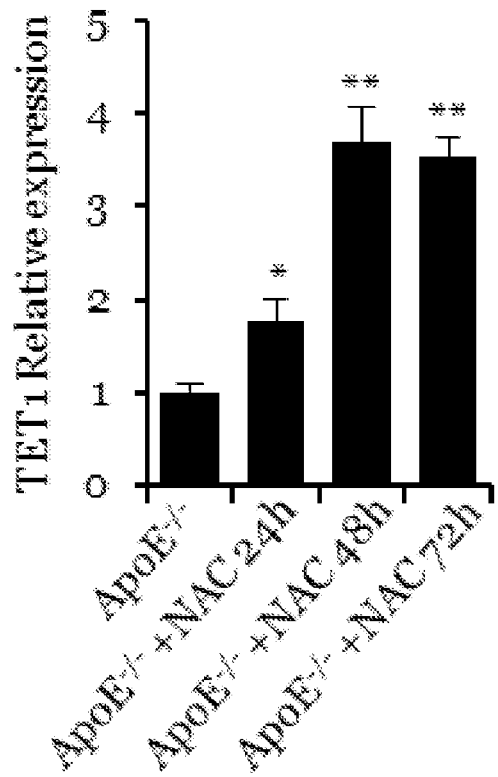

Ten eleven translocation (Tet) family, including Tet1, Tet2 and Tet3, demethylate genomic DNA (Ito et al., Nature. 466, 1129-33 (2010); Ko et al., Nature. 468, 839-43 (2010); Ito et al., Science, 333, 1300 (2011).). Within the Tet family, Tet2 has been shown to have a critical role in regulating the self-renewal, proliferation and differentiation of HSCs (Ko et al., Nature. 468, 839-43 (2010); Ko et al., Proc Natl Acad Sci USA. 108, 14566-71 (2011)), whereas the role of Tet1 in hematopoiesis is as yet unknown. In hematopoietic stem cells (HSC) of ApoE$^{-/-}$ mice we found a significant down-regulation of Tet1 (FIG. 1a). Supplemental treatment with NAC restored the expression of Tet1 in HSCs from ApoE$^{-/-}$ mice (FIG. 1b).

Figure 1C:
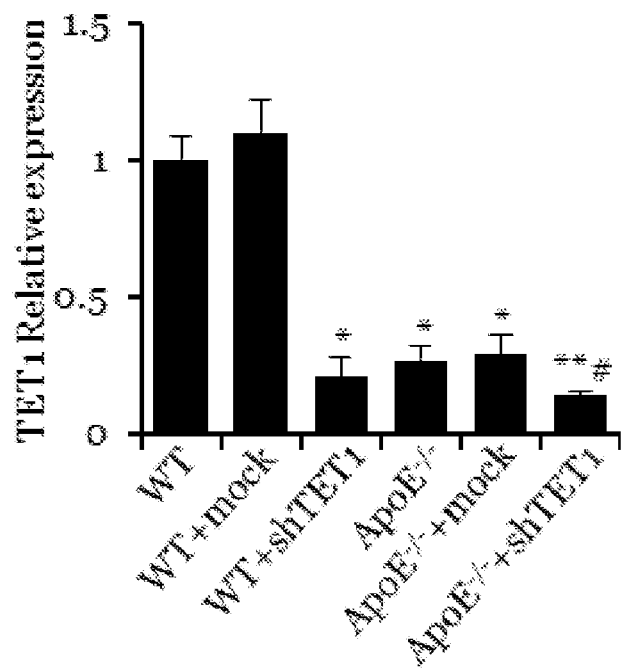
Figure 1D:
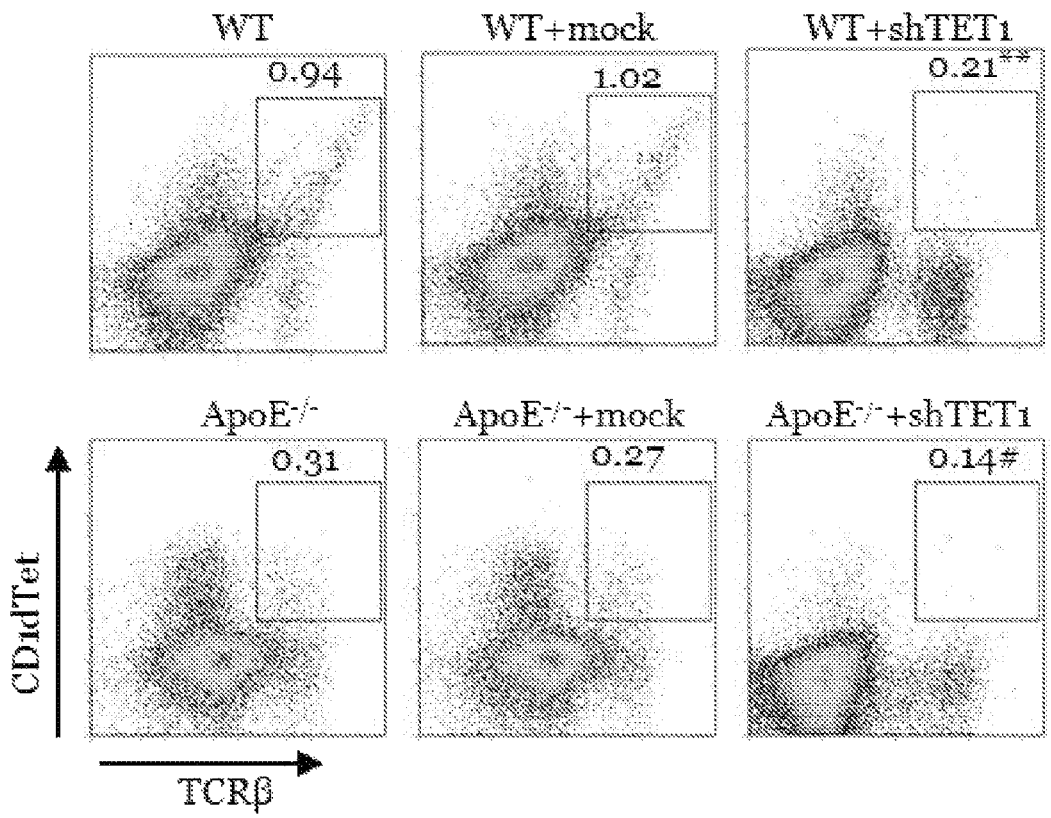
Figure 1E:
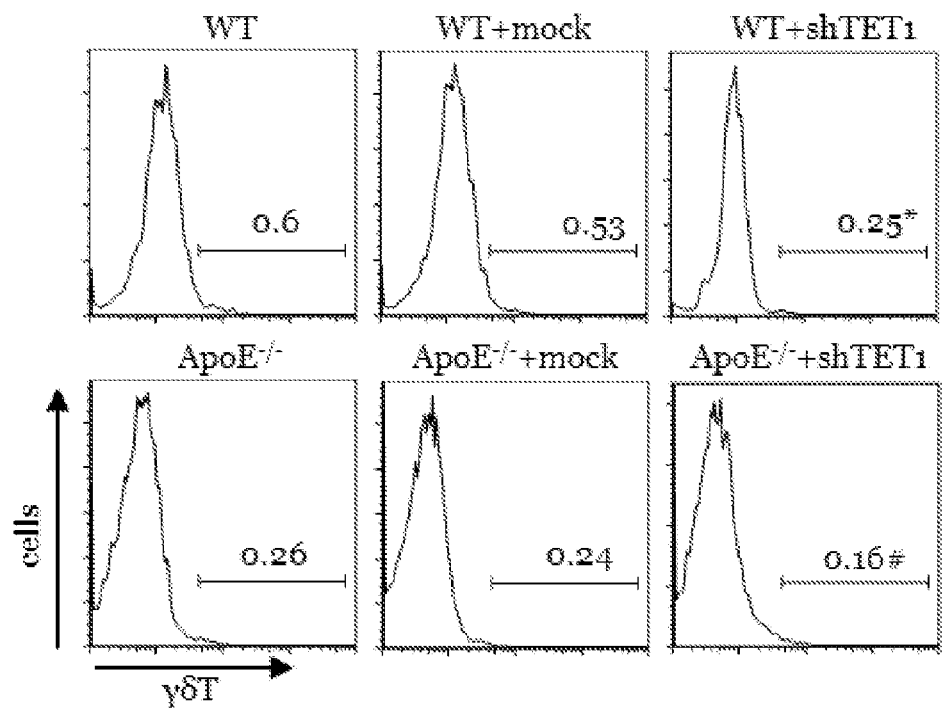
Figure 1F:
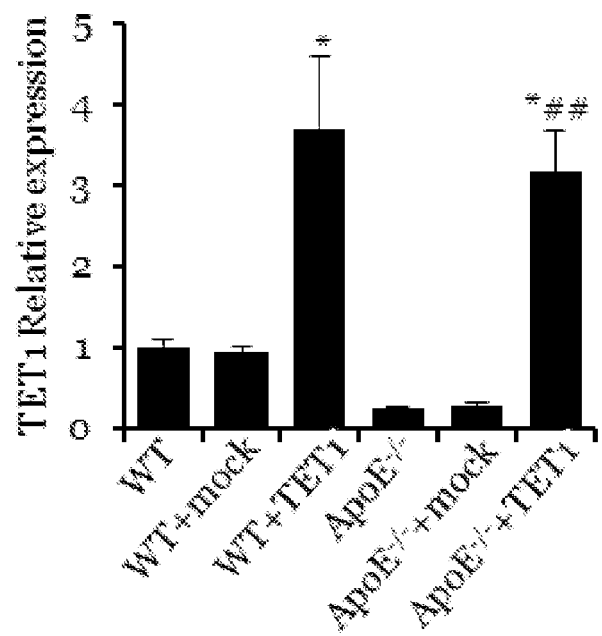
Figure 1G:
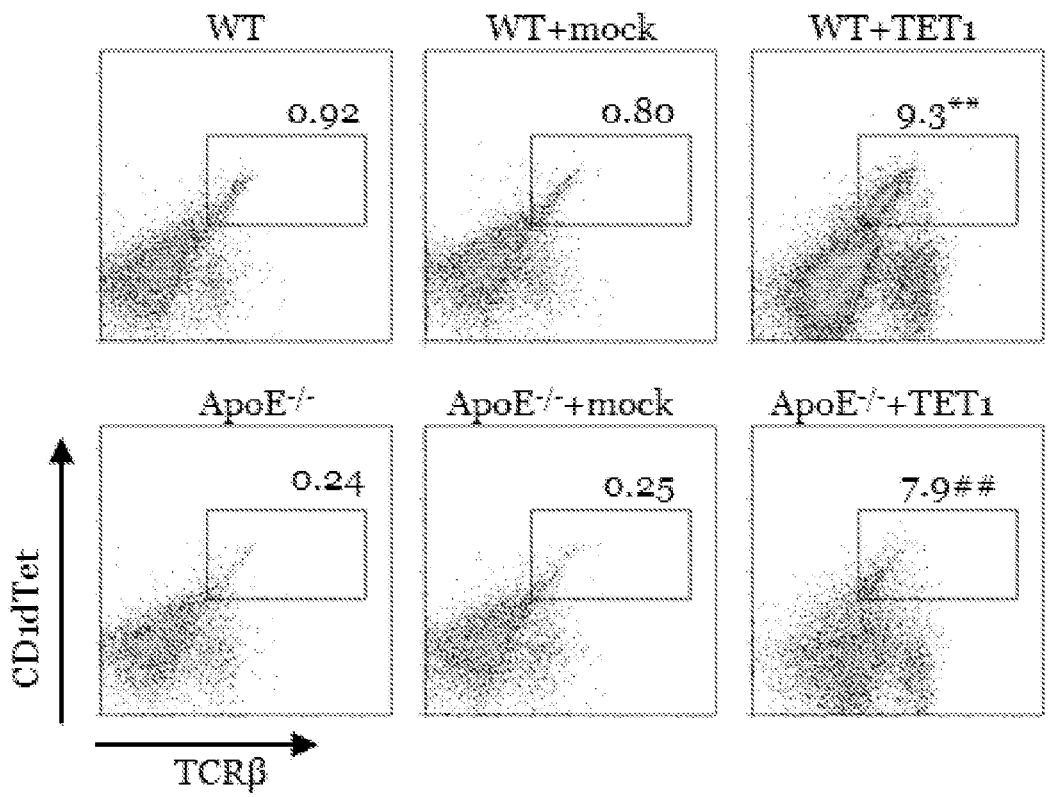
Figure 1H:
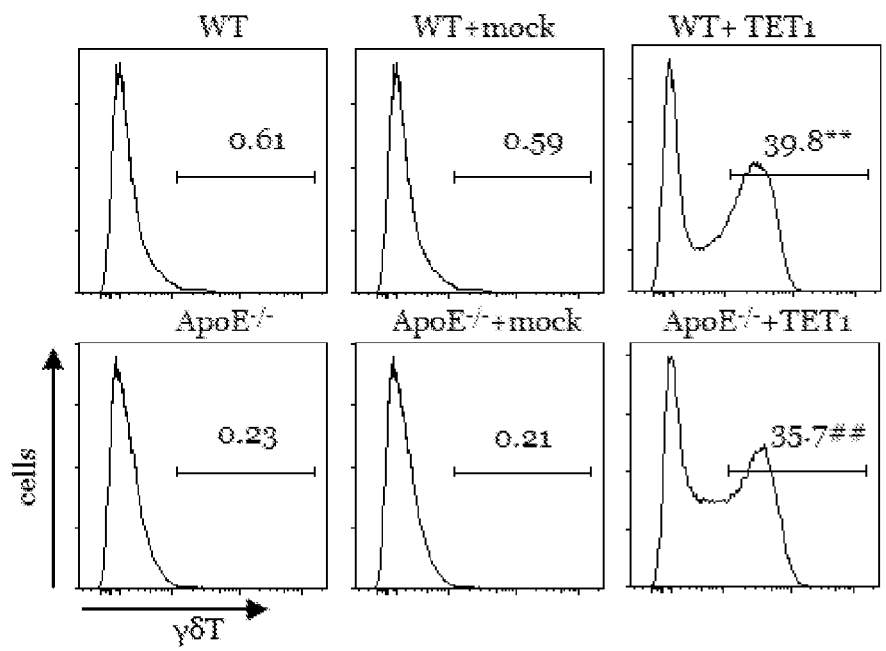
Figure 1I:
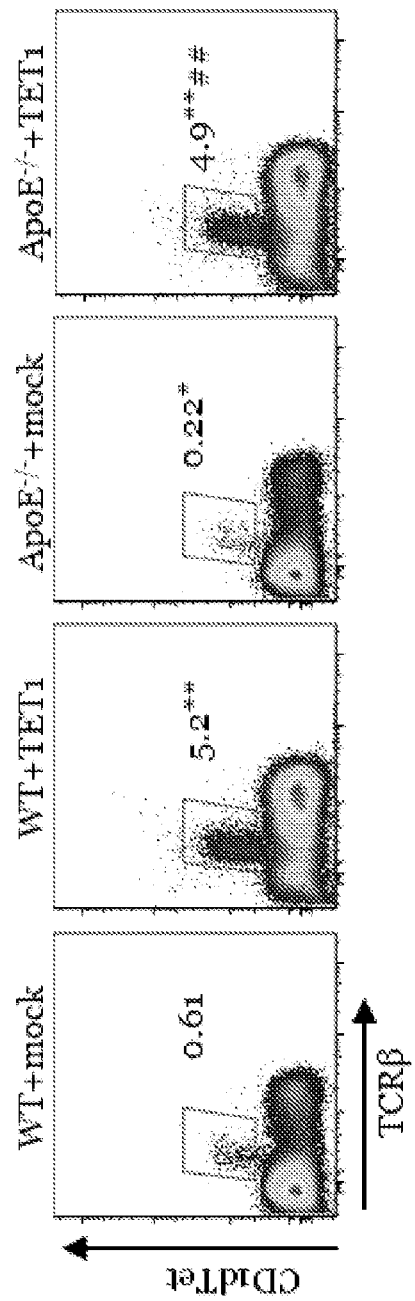
Figure 1J:
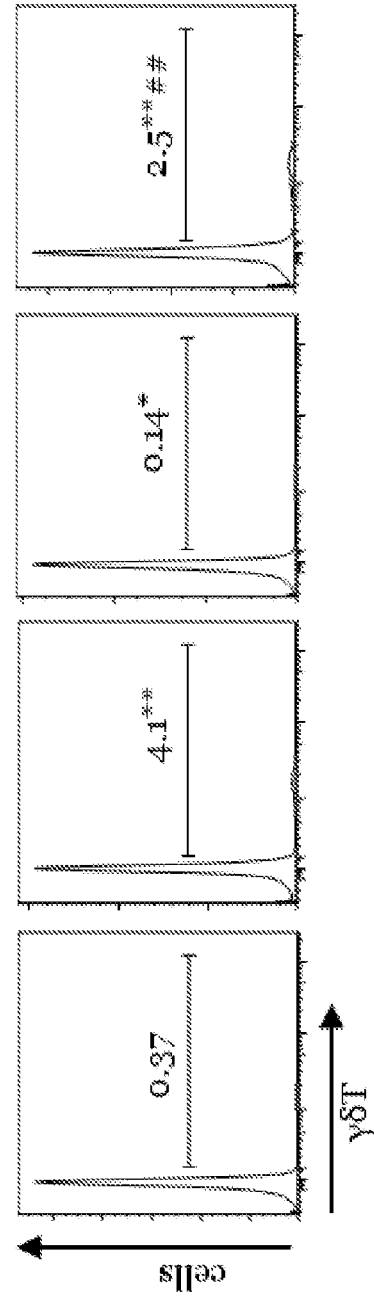

To test whether Tet1 plays a role in the differentiation of HSCs towards NKT and γδT cells, the expression of Tet1 in HSCs from WT and ApoE$^{-/-}$ mice was inhibited with shRNA (FIG. 1c). The inhibition of Tet1 in HSCs from both WT and ApoE$^{-/-}$ mice greatly reduced their differentiation towards NKT and γδT cells both in vivo and in vitro (FIGS. 1d, 1e). In contrast, the overexpression of Tet1 in HSCs from WT or ApoE$^{-/-}$ mice resulted in 6-10 fold increase in the differentiation towards NKT cells and more than 20 fold increase in their differentiation towards γδT cells (FIGS. 1f, 1g, 1h, 1i, 1j).

Figure 2A:
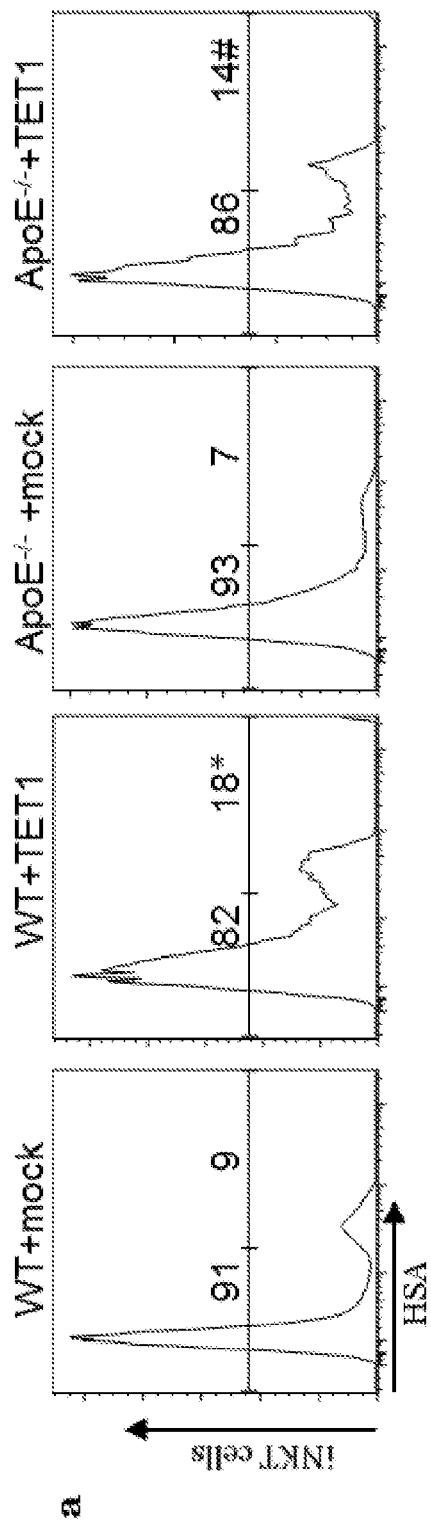
FIGS. 2a-e. The overexpression of TET1 alters the frequency of immature populations and specific subsets of NKT and γδT cells in vitro. a, HAS expression in NKT derived from in vitro co-culture. n=6, *, p<0.05, vs. WT+mock; #, p<0.05, vs. ApoE$^{-/-}$+mock. b, HAS expression in γδT cells derived from in vitro co-culture. n=6, *, p<0.05, vs. WT+mock; #, p<0.05, vs. ApoE$^{-/-}$+mock. c,d,e. V1 (c), V2 (d) and V6 (e) subsets in γδ T cells derived from in vitro co-culture of TET1 overexpressing HSCs. n=6, *, p<0.05, vs. WT+mock; #, p<0.05, vs. ApoE$^{-/-}$+mock.
Figure 2B:
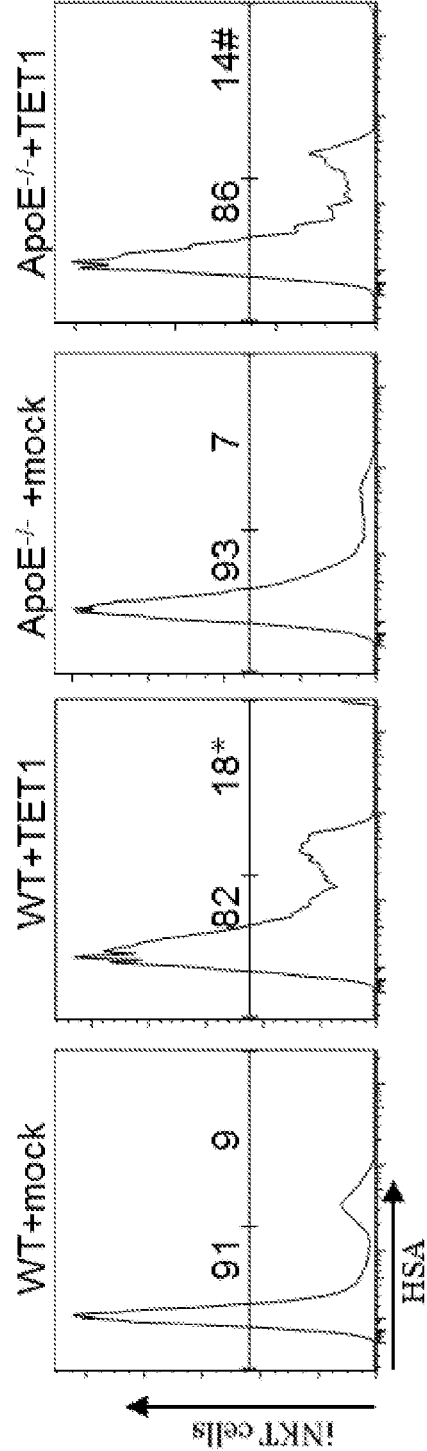
Figure 2C:
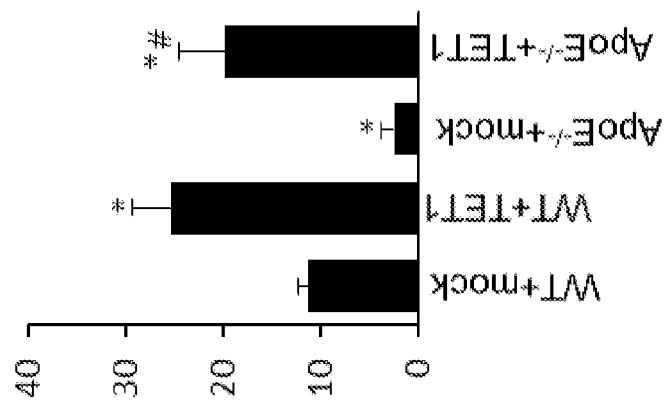
Figure 2D:
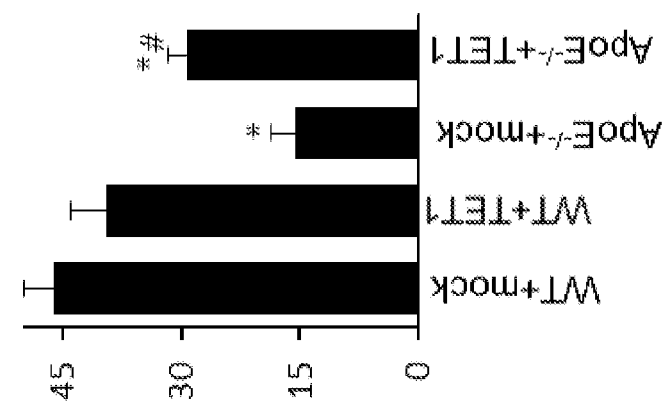
Figure 2E:
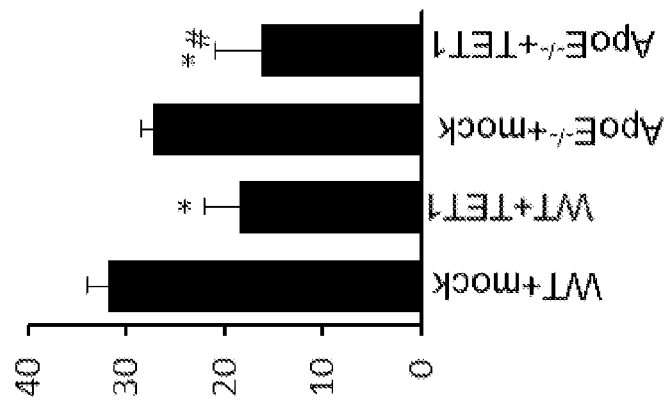
Figure 3A:
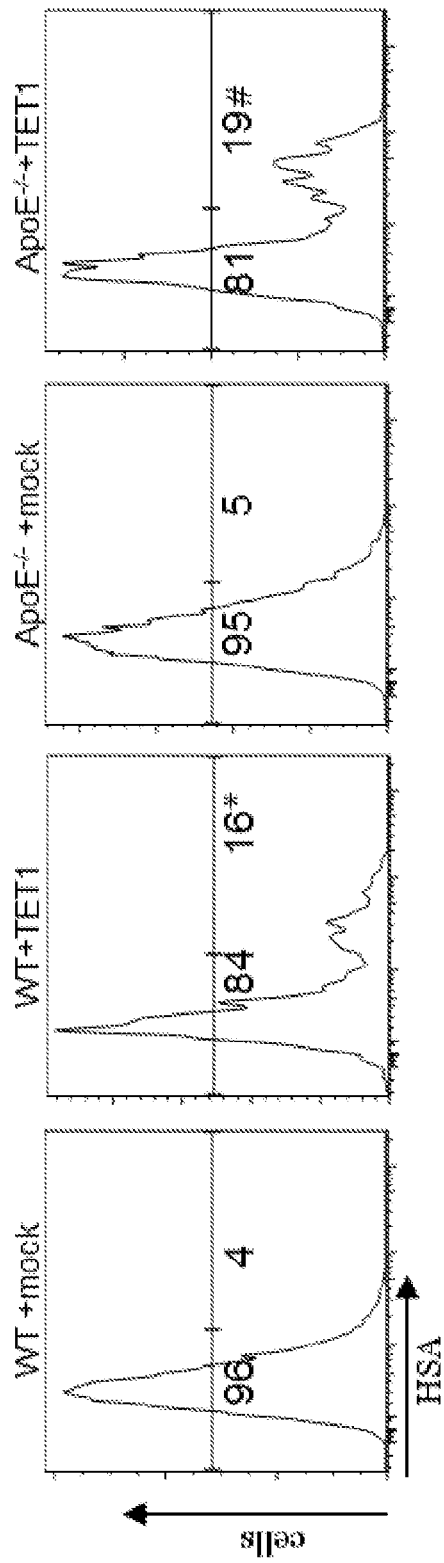
FIGS. 3a-g. The overexpression of TET1 alters the frequency of immature population and specific subsets of NKT and γδ T cells in vivo. a, HAS expression in NKT derived from in vitro co-culture. n=6, *, p<0.05, vs. WT+mock; #, p<0.05, vs. ApoE$^{-/-}$+mock. b, HAS expression in γδT cells derived from in vitro co-culture. n=6, *, p<0.05, vs. WT+mock; #, p<0.05, vs. ApoE$^{-/-}$+mock. c,d,e. V1 (c), V2 (d) and V6 (e) subsets in γδT cells derived from in vitro culture of TET1 overexpressing HSCs. n=6, *, p<0.05, vs. WT+mock; #, p<0.05, vs. ApoE$^{-/-}$+mock. f CCR6$^+$ population in γδT cells derived from recipient mice; g, IL-17$^+$ cells in γδT cells derived from recipient mice. n=8, *, p<0.05, vs. WT+mock; #, p<0.05, vs. ApoE$^{-/-}$+mock.
Figure 3B:
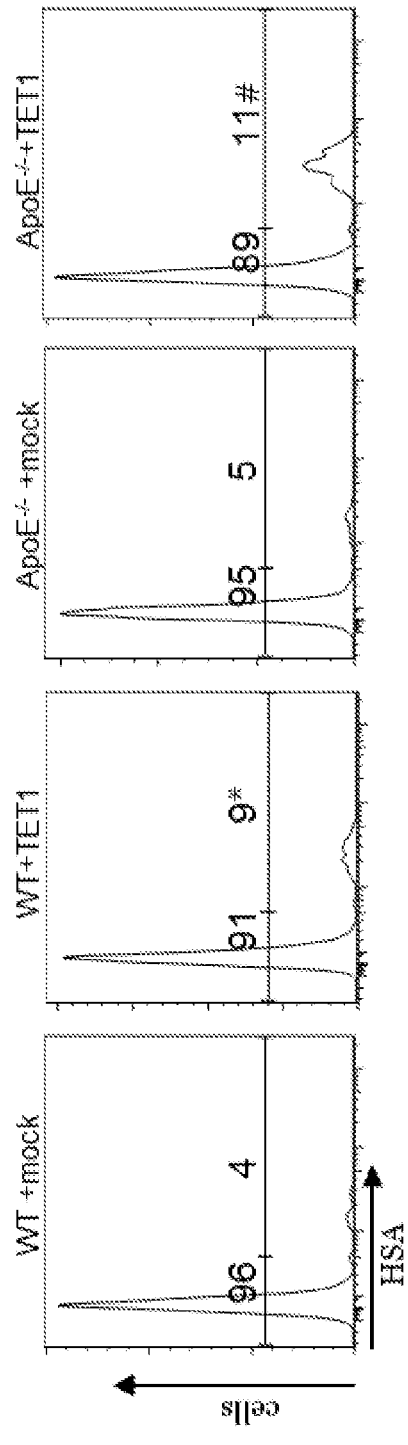
Figures 3C, 3D, 3E:
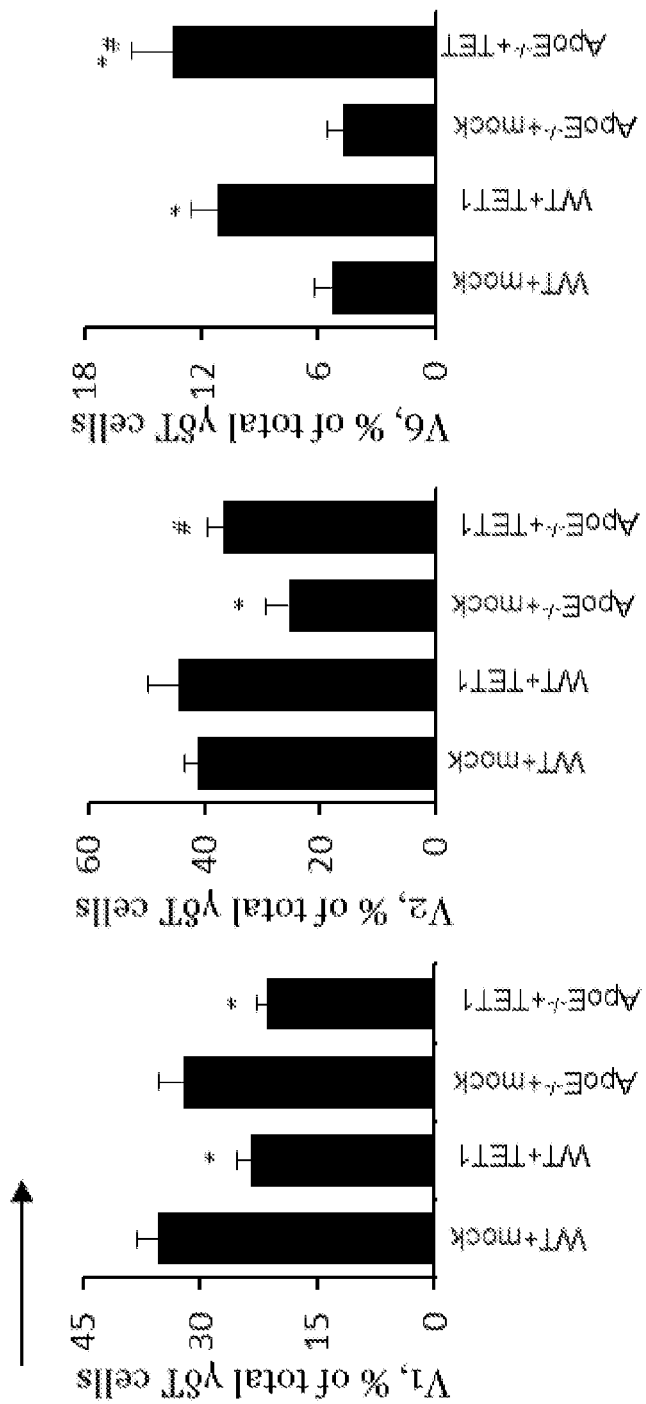
Figure 3G:
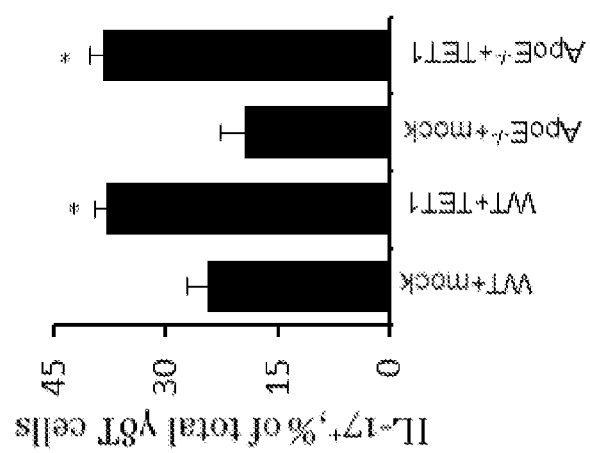
Figure 3F:
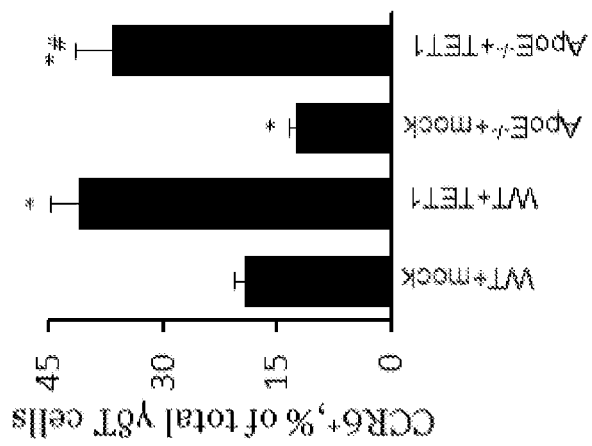
Figure 4:
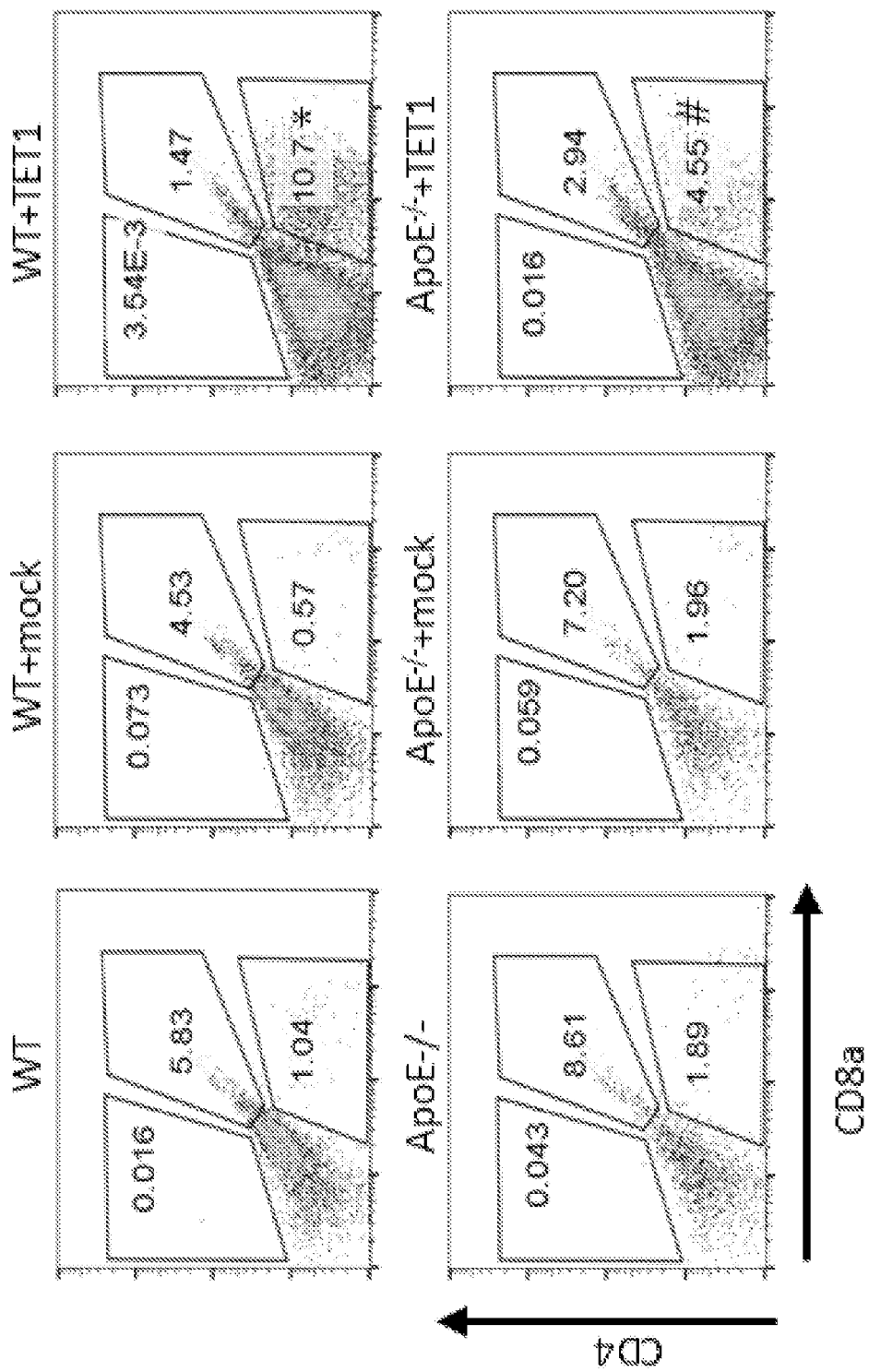
FIG. 4. The overexpression of TET1 alters the differentiation of CD4$^+$ and CD8$^+$ populations in in vitro co-culture of HSCs. n=8, *, p<0.05, vs. WT+mock; #, p<0.05, vs. ApoE$^{-/-}$+mock.

Both in vivo and in vitro, NKT and γδT cells derived from Tet1-overexpressing HSCs had greater staining for HSA, a cell surface marker that decreases in expression with maturation (FIGS. 2i, 2j; FIG. 3a, 3b). V1 subsets were decreased, while V2 and V6 subsets were significantly increased in γδ T cells derived from Tet1-overexpressing HSCs (FIGS. 2c, 2d, 2e; FIGS. 3c, 3d, 3e). Interestingly, γδT cells derived from Tet1 overexpressing HSCs displayed greater expression of CCR6 and IL-17 (FIG. 3f, 3g). Tet1 overexpression in HSCs also increased the differentiation towards CD8$^+$ T cells in in vitro differentiation assay (FIG. 4). These results indicate that Tet1 is a pivotal determinant of the differentiation of HSCs towards NKT and γδT cells as well as their function.

Figure 5C:
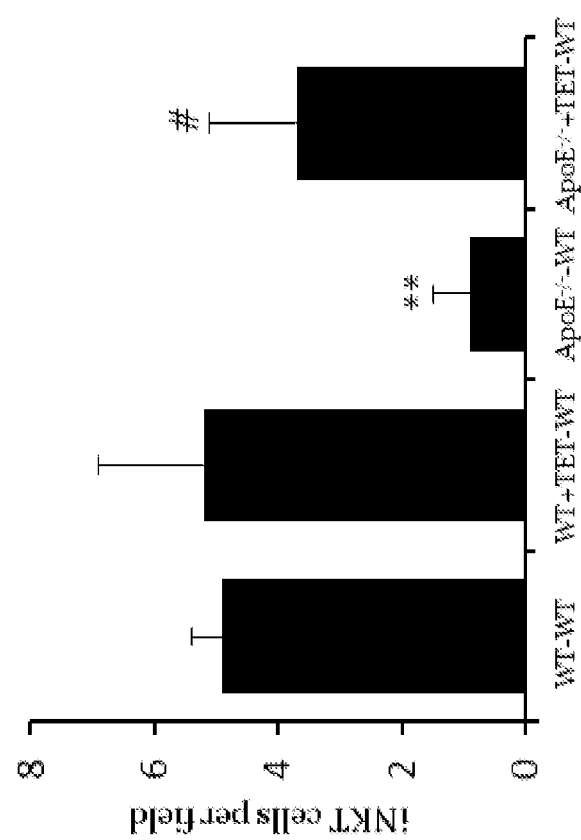
Figure 5D:
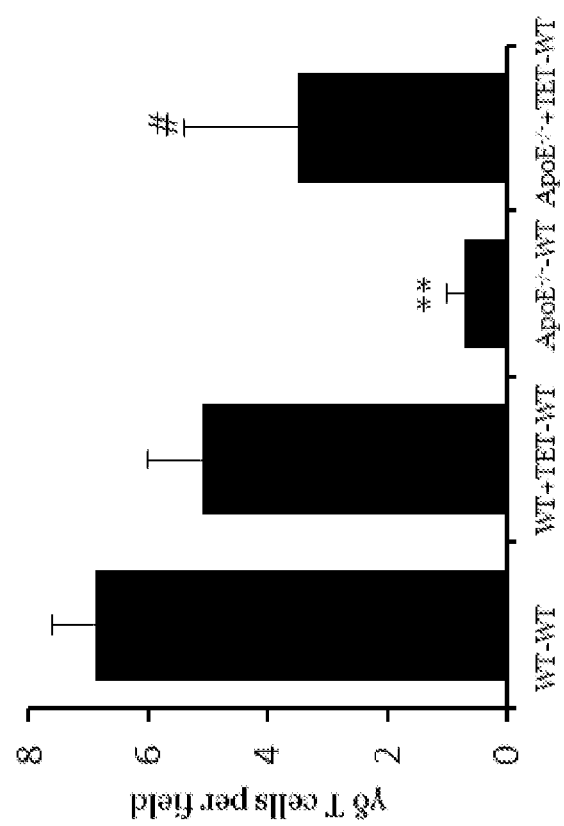
Figure 5E:
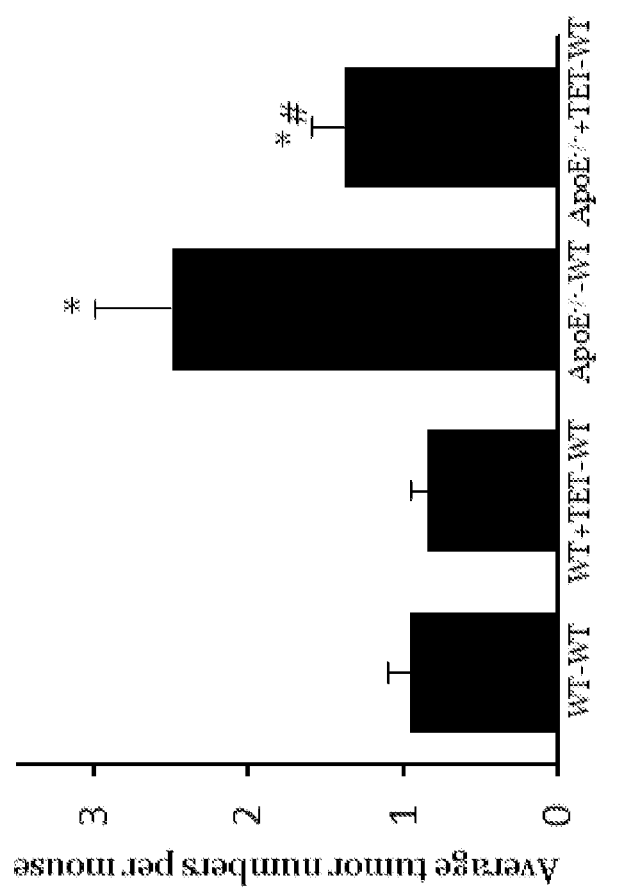
Figure 5F:
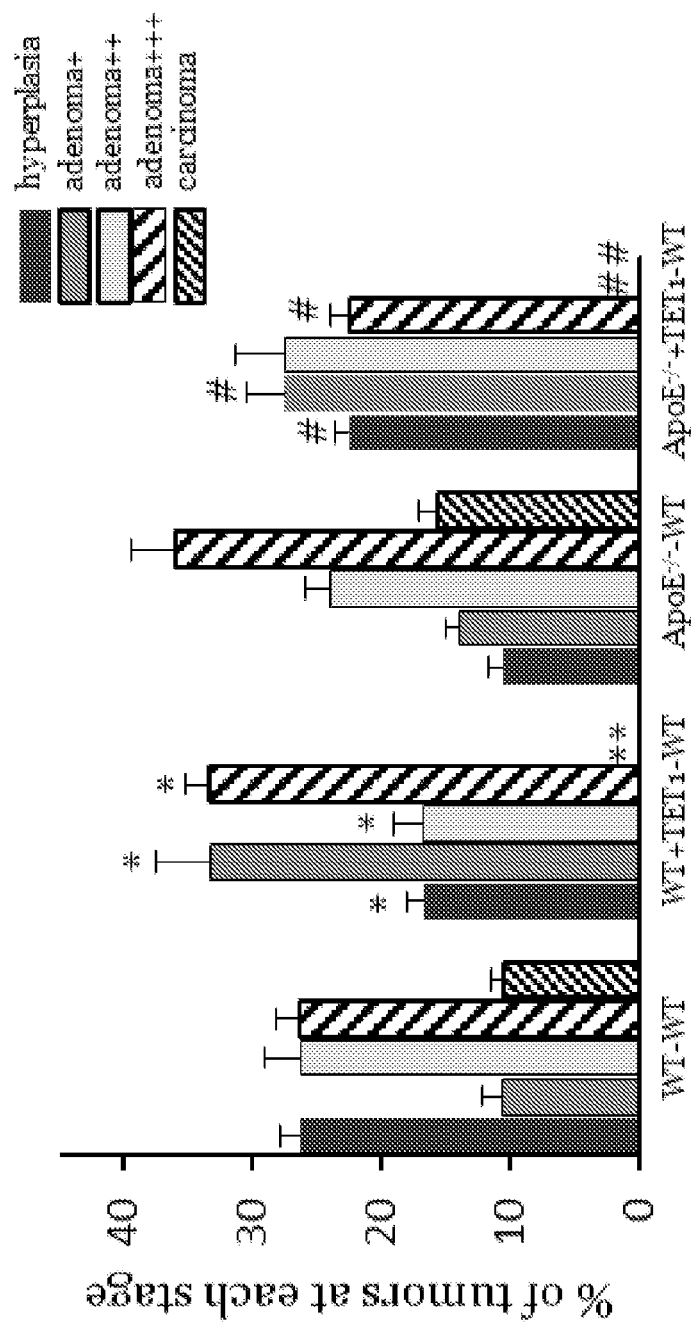

In order to determine whether the overexpression of Tet1 in HSCs could restore the impaired immunosurveillance against colorectal neoplasia observed in hypercholesterolemic mice, we reconstituted the hematopoiesis of lethally irradiated WT recipient mice with WT HSCs, Tet1-overexpressing HSCs, ApoE$^{-/-}$ HSCs or Tet1-overexpressing ApoE$^{-/-}$ HSCs. Because Tet1-overexpressing HSCs were extremely quiescent and not able to fully reconstitute the hematopoiesis in lethally irradiated WT recipient mice, the transplantation with Tet1-overexpressing WT HSCs was supported with WT HSCs and the transplantation of Tet1-overexpressing ApoE$^{-/-}$ HSCs was supported with ApoE$^{-/-}$ HSCs at the ratio of 3:1. NKT and γδT cell populations in thymus of the recipient mice reconstituted with Tet1-overexpressing ApoE$^{-/-}$ HSCs was significantly greater than those in the recipient mice with ApoE$^{-/-}$ HSCs (FIG. 5a, 5b). Similarly, the number of submucosal NKT and γδT cells were also significantly greater in the recipient mice reconstituted with Tet1-overexpressing ApoE$^{-/-}$ HSCs than those in the recipient mice reconstituted with ApoE$^{-/-}$ HSCs (FIG. 5c, 5d). In accordance with this increase in NKT and γδT cells, the average tumor number and histopathologic severity of colorectal neoplasia in the recipient mice reconstituted with Tet1-overexpressing ApoE$^{-/-}$ HSCs were significantly lower than those in the recipient mice with ApoE$^{-/-}$ HSC (FIGS. 5e, 5f). We also found that recipient mice reconstituted with Tet1-overexpressing WT HSCs had no carcinoma tumors (FIG. 5f). These results indicate that transplantation with Tet1-overexpressing HSCs normalizes NKT and γδT cell population and also restored immunosurveillance against colorectal neoplasia.

Example 2. Tet1 Epigenetically Regulates the Expression of Genes Critical in the Differentiation Toward NKT and γδT Cells The differentiation and maturation of NKT and γδ T cells is regulated by the strict control of gene expression (Matsuda and Gapin, Curr Opin Immunol. 17(2), 122-30 (2005); Garbe and von Boehmer, Trends Immunol. 28(3), 124-31 (2007)). To identify the molecular mechanisms that underlie the decreased differentiation of NKT and γδ T cells in hypercholesterolemic mice, we screened the expression of genes critical to the differentiation of HSCs towards NKT and γδ T cells in in vitro differentiation assay (Table 1). We found lower expression of Fyn, Sox13, IL-15R, ITK and SH2D1a in the cells derived from ApoE$^{-/-}$ HSCs than those from WT HSCs. Overexpression of Tet1 in ApoE$^{-/-}$ HSCs restored the expression of these genes to a level even greater than those from WT HSCs. The overexpression of Tet1 also increased the expression of ETV5, BCL11b, EGR2, SLAMF1, ZBTB16, RELb, PHF1 and NFKb1 in the cells derived from both WT HSCs and ApoE$^{-/-}$ HSCs. These results indicate that Tet1 exerts a heretofore unrecognized significant influence on the network of transcription factors and other genes that regulate the differentiation towards NKT and γδ T cells.

TABLE 1

| Genes related to iNKT cell differentiation | Genes related to γδ T cell differentiation |
|---|---|
| Interleukin-2 receptor β (IL-2Rb) | B-cell lymphoma/leukemia 11B (BCL11b) |
| Interleukin-15 receptor (IL-15R) | Early growth response protein 2 (EGR2) |
| E26 Transformation specific transcription factor 1 (Ets1) | Ets variant 5 (ETV5) |
| myeloid Elf-1-like factor (MEF) | inhibitor of DNA binding protein 2 (ID2) |
| Interferon regulatory factor 1 (IRF-1) | inhibitor of DNA binding protein 3 (ID3) |
| Fyn | interleukin-2-inducible T-cell kinase (ITK) |
| interleukin-2-inducible T-cell kinase (Itk) | Iterleukin 7 receptor (IL-7R) |
| Activator protein-1 (AP-1) | Interleukine-15 receptor (IL-15R) |
| T cell factor 1 (TCF-1) | PHD finger protein 1 (PHF1) |
| Nuclear factor κB p50 (NFκb) | SLAM-Associated Protein (SAP, SH2D1a) |
| RELb | Sry-related HMG box 13 (Sox13) |
| IκB kinase 2 (IKK2) | T cell factor 12 (TCF12) |
| Protein kinase C-θ (PKCθ) | Zinc finger and BTB domain-containing protein 16 (ZBTB16) |
| Signaling lymphocytic activation molecule F1 (SLAMF1) | |
| signaling lymphocytic activation molecule-associated protein (SAP) | |
| Krüppel-like factor 2 (KLF2) | |
| CCR9 | |

Thus, we have exposed human normal HSCs to oxidized-LDL and have shown a concentration-dependent impairment of their differentiation toward NKT and γδ T cells. In addition, exposure of human HSCs to oxidized-LDL also downregulates Tet1 as it does in mouse HSCs. Specifically, HC causes an oxidant-stress dependent downregulation of Tet1 in HSCs that reduces the expression of genes critical for γδ T cell and NKT cell differentiation. These effects reduce the concentration of γδ T cells and NKT cells in colon submucosa and at the early stages of tumor development and thereby impair immunosurveillance against colorectal neoplasia. Overexpression of Tet1 in HSCs of HC mice restores their differentiation toward NKT and γδ T cells and reverses the increased incidence of colorectal neoplasia.

The results above showed that Tet1 is a crucial and essential determinant in the differentiation from HSCs towards NKT and γδ T cells as well as a pivotal role in the mechanism by which HC increases the incidence of colorectal neoplasia. The overexpression of Tet1 in HSCs dramatically increased the differentiation of HSCs towards NKT and γδ T cells both in vitro and in vivo.

Example 3. Establishing In Vitro and In Vivo Systems to Enhance the Differentiation of Human HSCs Towards NKT and γδ T Cells Given that the Tet protein family is highly conserved in mammals, it was hypothesized that Tet1 also functions as a determinant in the differentiation of human HSCs to NKT and γδ T cells. To test this hypothesis, we will clone the full length human Tet1 or the catalytic domain of human Tet1 into lentiviral vectors. The lentiviral constructs yield among the best outcome to introduce DNA fragments or genes into human HSCs. Normal human HSCs and Tet1 overexpressing human HSCs will be selected and co-cultured with support cells which consistently express the critical molecule for T cell differentiation, Notch ligand Delta-like 1. The co-culture system is a reliable assay to study the in vitro differentiation of HSCs towards T cell lineages. It has been repeatedly used in numerous laboratories. The percentage of NKT and γδ T cells in the co-culture will be determined by flow cytometry 6-8 weeks following viral transduction. In the in vivo experiments, normal human HSCs or human HSCs overexpressing Tet1 will be injected intravenously (at a dose of $5\times10^3$) into three month old lethally irradiated NOD-scid IL2rγ$^{null}$ (NSG) humanized mice. The frequency of NKT and γδ T cells derived from human HSCs will be closely monitored at multiple time points after transplantation. In these experiments, we will measure the subsets of NKT and γδ T cells derived from normal human HSCs and Tet1 overexpressing human HSCs as well as the critical molecules and cytokines which are fundamental for the function of NKT and γδ T cells.

Example 4. Determining Tet1-Dependent Epigenetic Regulation in the Differentiation of Human HSCs Towards NKT and γδ T Cells Current hematological research is raising the concern that even a highly enriched HSC fraction is heterogeneous in terms of lymphopoietic potential. Heritable epigenetic signatures of DNA, histone and chromosome conformation, appear to have a major role in the process (18, 19). Although the regulatory network governing the differentiation of HSCs towards NKT and γδ T cells has been extensively explored in the last decades, the epigenetic signature predisposing HSCs towards NKT and γδ T cell fate is yet unknown.

Tet-dependent DNA demethylation results in open chromatin structure and permits the transcription of target genes (Ko et al., Proc Natl Acad Sci USA. 108, 14566-71 (2011); Wu and Zhang, Genes Dev. 25(23), 2436-52 (2011)). Pyrosequencing analysis showed that Fyn, Sox13, IL-15R, EGR2 and SH2D1a were highly methylated in the cells derived from ApoE$^{-/-}$ HSCs, supporting a Tet1-dependent downregulation of the genes. The overexpression of Tet1 significantly decreased the methylation of most targeted genes in the cells derived from both WT and ApoE$^{-/-}$ HSCs, which correlates well with the high expression of the targeted genes in the cells derived from Tet1 overexpressing HSCs. These results indicate that Tet1-dependent demethylation regulates the expression of targeted genes that mediate HSC differentiation toward NKT and γδT cells.

However, we also found that the expression of BCL11b, RELb and PHF1 was increased in the cells derived from Tet1 overexpressing HSCs, but their methylation status was unchanged. In addition, although the methylation of ETV5, EGR2, RELb and NEKB1 was significantly higher in the cells derived from ApoE$^{-/-}$ HSCs than those from WT HSCs, their expression was unchanged, indicating that the regulation of the genes responsible for NKT and γδT cell differentiation is more complex.

Recent studies indicate that Tet proteins may also participate in the regulation of histone modification via distinct pathways. The O-linked N-acetylglucosamine (O-GlaNAc) transferase OGT is an evolutionarily conserved enzyme that catalyzes O-linked protein glycosylation. Tet proteins were identified as stable partners of OGT in the nucleus (Vella et al., Mol Cell. 49(4), 645-56 (2013); Chen et al., Nature. 493(7433), 561-4 (2013); Shi et al., J Biol Chem. 288(29), 20776-84 (2013)). The interaction of Tet2 and Tet3 with OGT led to the GlcNAcylation of Host Cell Factor 1 and the integrity of H3K4 methyltransferase SET1/COMPASS complex, indicating that Tet proteins increase H3K4me3 that induces transcriptional activation (Deplus et al., EMBO J. 32(5), 645-55 (2013)). Although an early observation showed that the interaction between Tet1 and OGT was limited to embryonic stem cells (Bendelac et al., Annu Rev Immunol. 25, 297-336 (2007)), our immunoprecipitation studies indicate that OGT also has strong interactions with Tet1 in HSCs. In accordance with the decrease in Tet1 expression, the interaction with OGT was significantly reduced in HSCs isolated from hypercholesterolemic mice. The overexpression of Tet1 significantly increased the interaction of Tet1 and OGT, but did not influence the expression and interaction of Tet3 and OGT in the cells. H3K4me3 modification in all the genes except RELb and NFKB1 was increased after Tet1 overexpression, suggesting that by interacting with OGT Tet1 plays an important role in H3K4me3 modification in HSCs.

Our study showed that Tet1 increased the expression of genes critical in the differentiation of HSCs towards NKT and γδ T cells in mouse by demethylating the genes responsible for the differentiation from HSCs. We also have evidence that Tet1 also regulates the expression of genes by inducing histone protein modifications, primarily of H3K27me3 and H3K4me3. We harvest the T cells derived from normal human HSCs and Tet1 overexpressing human HSCs, and screen the expression of genes crucial in the differentiation of human HSCs towards NKT and γδ T cells. Then, we measure the DNA methylation status of these genes by using pyrosequencing, and measure H3K27me 3 and H3K4me3 as well as other histone modifications by using ChIP-PCR.

Example 5. The Use of NKT and γδ T Cells Derived from Tet1 Overexpressing HSCs in Cancer Immunotherapy We will apply two different approaches to demonstrate the use of NKT and γδ T cells derived from Tet1 overexpressing human HSCs. In the first approach, we will generate and purify NKT and γδ T cells in the in vitro co-culture system and inject them into NSG humanized mice which would have been implanted with human colorectal tumors. The cancer burden and the infiltration of NKT and γδ T cells derived from Tet1 overexpressing human HSCs into tumors will be determined at multiple time points. Furthermore, we will determine the capacity of these NKT and γδ T cells to recognize and eliminate cancer cells in vitro. In the second approach, we will reconstitute the hematopoiesis of lethally irradiated NSG mice with normal human HSCs or Tet1 overexpressing human HSCs. Then, human colorectal cancer tissue will be implanted in the chimeric mice. The frequency of NKT and γδ T cells in peripheral blood will be closely monitored. The cancer burden and the infiltration of NKT and γδ T cells derived from Tet1 overexpressing human HSCs into tumors will be determined at multiple time points.

REFERENCES

1. Lantz O, Bendelac A. An invariant T cell receptor alpha chain is used by a unique subset of major histocompatibility complex class I-specific CD4+ and CD4-8-T cells in mice and humans. J Exp Med. 1994. 180(3):1097-106.

2. Porcelli S, Yockey C E, Brenner M B, Balk S P. Analysis of T cell antigen receptor (TCR) expression by human peripheral blood CD4-8-alpha/beta T cells demonstrates preferential use of several V beta genes and an invariant TCR alpha chain. J Exp Med. 1993. 178(1):1-16.

3. Smyth M J, Thia K Y, Street S E, Cretney E, Trapani J A, Taniguchi M, Kawano T, Pelikan S B, Crowe N Y, Godfrey D I. Differential tumor surveillance by natural killer (NK) and NKT cells. J Exp Med. 2000. 191(4):661-8.

4. Crowe N Y, Smyth M J, Godfrey D I. A critical role for natural killer T cells in immunosurveillance of methylcholanthrene-induced sarcomas. J Exp Med. 2002. 196(1): 119-27.

5. Gomes A Q[1], Martins D S, Silva-Santos B. Targeting γδ T lymphocytes for cancer immunotherapy: from novel mechanistic insight to clinical application. Cancer Res. 2010.70(24):10024-7.

6. Toura I, Kawano T, Akutsu Y, Nakayama T, Ochiai T, Taniguchi M. Cutting edge: inhibition of experimental tumor metastasis by dendritic cells pulsed with alpha-galactosylceramide. J Immunol. 1999.163(5):2387-91.

7. Bennouna J, Levy V, Sicard H, Senellart H, Audrain M, Hiret S, Rolland F, Bruzzoni-Giovanelli H, Rimbert M, Galéa C, Tiollier J, Calvo F. Phase I study of bromohydrin pyrophosphate (BrHPP, IPH 1101), a Vgamma9Vdelta2 T lymphocyte agonist in patients with solid tumors. Cancer Immunol Immunother. 2010.59(10):1521-30.

8. Kobayashi H, Tanaka Y, Yagi J, Osaka Y, Nakazawa H, Uchiyama T, Minato N, Toma H. Safety profile and antitumor effects of adoptive immunotherapy using gammadelta T cells against advanced renal cell carcinoma: a pilot study. Cancer Immunol Immunother. 2007. 56(4):469-76.

9. Kobayashi H, Tanaka Y, Nakazawa H, Yagi J, Minato N, Tanabe K. A new indicator of favorable prognosis in locally advanced renal cell carcinomas: gamma delta T-cells in peripheral blood. Anticancer Res. 2011.31(3):1027-31.

10. Kondo M, Sakuta K, Noguchi A, Ariyoshi N, Sato K, Sato S, Sato K, Hosoi A, Nakajima J, Yoshida Y, Shiraishi K, Nakagawa K, Kakimi K Zoledronate facilitates large-scale ex vivo expansion of functional gammadelta T cells from cancer patients for use in adoptive immunotherapy. Cytotherapy. 2008; 10(8):842-56.

11. Motohashi S, Ishikawa A, Ishikawa E, Otsuji M, Iizasa T, Hanaoka H, Shimizu N, Horiguchi S, Okamoto Y, Fujii S, Taniguchi M, Fujisawa T, Nakayama T. A phase I study of in vitro expanded natural killer T cells in patients with advanced and recurrent non-small cell lung cancer. Clin Cancer Res. 2006. 15; 12(20 Pt 1):6079-86.

12. Watarai H, Fujii S, Yamada D, Rybouchkin A, Sakata S, Nagata Y, Iida-Kobayashi M, Sekine-Kondo E, Shimizu K, Shozaki Y, Sharif J, Matsuda M, Mochiduki S, Hasegawa T, Kitahara G, Endo T A, Toyoda T, Ohara O, Harigaya K, Koseki H, Taniguchi M. Murine induced pluripotent stem cells can be derived from and differentiate into natural killer T cells. J Clin Invest. 2010.120(7):2610-8.

13. Themeli M, Kloss C C, Ciriello G, Fedorov V D, Perna F, Gonen M, Sadelain M. Generation of tumor-targeted human T lymphocytes from induced pluripotent stem cells for cancer therapy. Nat Biotechnol. 2013.31(10):928-33.

14. Ito S, D'Alessio A C, Taranova O V, Hong K, Sowers L C, Zhang Y. Role of Tet proteins in 5 mC to 5 hmC conversion, ES-cell self-renewal and inner cell mass specification. Nature. 2010. 466(7310):1129-33.

15. Ko M, Huang Y, Jankowska A M, Pape U J, Tahiliani M, Bandukwala H S, An J, Lamperti E D, Koh K P, Ganetzky R, Liu X S, Aravind L, Agarwal S, Maciejewski J P, Rao A. Impaired hydroxylation of 5-methylcytosine in myeloid cancers with mutant TET2. Nature. 2010.468(7325):839-43.

16. Ito S, Shen L, Dai Q, Wu S C, Collins L B, Swenberg J A, He C, Zhang Y. Tet proteins can convert 5-methylcytosine to 5-formylcytosine and 5-carboxylcytosine. Science. 2011. 333(6047):1300-3.

17. Ko M, Bandukwala H S, An J, Lamperti E D, Thompson E C, Hastie R, Tsangaratou A, Rajewsky K, Koralov S B, Rao A.Ten-Eleven-Translocation 2 (TET2) negatively regulates homeostasis and differentiation of hematopoietic stem cells in mice. Proc Natl Acad Sci USA. 2011.108(35):14566-71

18. Cullen S M, Mayle A, Rossi L, Goodell M A. Hematopoietic stem cell development: an epigenetic journey. Curr Top Dev Biol. 2014.107:39-75

19. Yokota T, Sudo T, Ishibashi T, Doi Y, Ichii M, Orirani K, Kanakura Y. Complementary regulation of early B-lymphoid differentiation by genetic and epigenetic mechanisms. Int J Hematol. 2013. 98(4):382-9.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of preparing a population of Natural Killer T cells (NKT) and/or γδ T cells, the method comprising:
   obtaining a first population comprising hematopoietic stem cells (HSC);
   engineering the HSC to overexpress Ten eleven translocation (Tet)1;
   maintaining the Tet1-overexpressing HSC in culture under conditions and for a time sufficient for at least some of the HSC to differentiate into NKT and/or γδ T cells; and
   optionally purifying the NKT and/or γδ T cells,
   thereby providing a population of NKT and/or γδ T cells.

2. The method of claim 1, wherein the first population comprising HSC is obtained from the subject who has cancer.

3. The method of claim 1, wherein the Tet1-overexpressing HSC overexpress exogenous Tet1.

4. The method of claim 1, wherein the Tet1-overexpressing HSC comprise a Tet1 gene operably linked to a regulatory region other than the endogenous Tet1 regulatory region.

5. The method of claim 2, wherein the cancer is colon cancer, ovarian cancer, prostate cancer, lymphoid malignancies, myeloma, renal cell carcinoma, breast cancer, or malignant glioma.

6. The method of claim 2, wherein the subject has carcinoma, sarcoma, myeloma, leukemia, or lymphoma.

* * * * *